(12) United States Patent
Ren et al.

(10) Patent No.: US 10,214,783 B2
(45) Date of Patent: Feb. 26, 2019

(54) ENDPOINT ZYGOSITY ASSAY TO DETECT RF4 GENE IN MAIZE

(71) Applicant: Dow AgroSciences LLC, Indianapolis, IN (US)

(72) Inventors: Ruihua Ren, Carmel, IN (US); Peizhong Zheng, Carmel, IN (US); Siva Prasad Kumpatla, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/948,271

(22) Filed: Jul. 23, 2013

(65) Prior Publication Data

US 2014/0024037 A1 Jan. 23, 2014
US 2016/0355894 A9 Dec. 8, 2016

Related U.S. Application Data

(63) Continuation-in-part of application No. 13/244,049, filed on Sep. 23, 2011, now Pat. No. 10,117,411.

(60) Provisional application No. 61/674,556, filed on Jul. 23, 2012, provisional application No. 61/390,526, filed on Oct. 6, 2010.

(51) Int. Cl.
*C12Q 1/68* (2018.01)
*C12Q 1/6895* (2018.01)

(52) U.S. Cl.
CPC ....... *C12Q 1/6895* (2013.01); *C12Q 2600/13* (2013.01); *C12Q 2600/156* (2013.01)

(58) Field of Classification Search
USPC ....................................... 435/6.12
See application file for complete search history.

(56) References Cited

U.S. PATENT DOCUMENTS

2011/0151441 A1* 6/2011 Chen et al. .................. 435/6
2012/0090047 A1* 4/2012 Ren et al. .................... 800/267

FOREIGN PATENT DOCUMENTS

WO WO 2011/075648 6/2011
WO WO 2011/143344 11/2011
WO WO 2012/047595 4/2012

OTHER PUBLICATIONS

Genbank Accession No. XM_002457661—Sorghum bicolor hypothetical protein, mRNA (GI: 242057120, submitted by Paterson et al. Sep. 27, 2008, retrieved on Apr. 24, 2014 from http://www.ncbi.nlm.nih.gov/nuccore/GI:242057120).*
Bubner B, Baldwin IT. Use of real-time PCR for determining copy number and zygosity in transgenic plants. Plant Cell Rep. Nov. 2004; 23(5):263-71. Epub Sep. 11, 2004. Review.*
Bubner B, Gase K, Baldwin IT. Two-fold differences are the detection limit for determining transgene copy numbers in plants by real-time PCR. BMC Biotechnol. Jul. 13, 2004; 4:14.*
Yang L, Guo J, Pan A, Zhang H, Zhang K, Wang Z, Zhang D. Event-specific quantitative detection of nine genetically modified maizes using one novel standard reference molecule. J Agric Food Chem. Jan. 10, 2007; 55(1):15-24.*
Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*
Cho et al., "Determination of cytoplasmic male sterility factors in onion plants (*Allium cepa* L.) using OCR-RFLP and SNP markers," *Molecules and Cells*, 2006; 21(3):411-417.
International Search Report and Written Opinion for PCT/US2013/51622 dated Oct. 10, 2013 (Oct. 10, 2013).

* cited by examiner

*Primary Examiner* — Gary Benzion
*Assistant Examiner* — Olayinka A Oyeyemi
(74) *Attorney, Agent, or Firm* — Barnes & Thornburg LLP (Dow)

(57) ABSTRACT

A method is provided for determining the zygosity of an Rf4 gene in a corn plant. A method may include performing a first PCR assay, a second PCR assay, quantifying probes used in the first and second PCR assays, and comparing the quantified probes to determine zygosity.

37 Claims, 3 Drawing Sheets

Specification includes a Sequence Listing.

ENDPOINT ZYGOSITY ASSAY TO DETECT RF4 GENE IN MAIZE

CROSS-REFERENCE TO RELATED APPLICATIONS

This application claims the benefit of priority under 35 U.S.C. § 119(e) of U.S. Provisional Application Ser. No. 61/674,556, filed on Jul. 23, 2012, the entire disclosure of which is incorporated herein by reference. This application is also a continuation-in-part of U.S. patent application Ser. No. 13/244,049, filed on Sep. 23, 2011, which claims the benefit of priority of U.S. Provisional Application Ser. No. 61/390,526, filed on Oct. 6, 2010, the entire disclosures of both which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 22, 2013, is named 6257-225987_SL.txt and is 28,606 bytes in size.

BACKGROUND

Cytoplasmic male sterility (CMS) is a maternally inherited inability to produce functional pollen and has been successfully used in commercial production of hybrid seed, avoiding the drawbacks of hand or mechanical emasculation (Kaul, 1988). Breeders produce hybrid seed using a CMS system by developing female lines that carry CMS cytoplasm but lack restorer genes and by developing male lines that carry the appropriate restorer genes. F1 hybrid seed produced by the female lines carry the CMS cytoplasm but yield fertile plants because of the action of the paternally contributed nuclear restorer genes.

More than 40 sources of CMS have been found in maize and were classified into three major groups by differential fertility restoration reactions. These groups are designated as CMS-T (Texas), CMS-S (USDA) and CMS-C (Charrua) (Beckett 1971). In the CMS-T group, two dominant genes, Rf1 and Rf2, located on chromosomes 3 and 9, respectively, are required for the restoration of pollen fertility (Duvick 1965). The S-cytoplasm is restored by a single gene, Rf3 on chromosome 2 (Laughnan and Gabay 1978).

Rf genes have been cloned or mapped to high resolutions from several plant species, for example, Rf2 from maize (*Zea mays*) (Cui et al., 1996), Rf-PPR592 from *Petunia* (*Petunia hybrida*) (Bentolila et al., 2002), Rfo from radish (*Raphanus sativus*) (Brown et al., 2003; Desloire et al., 2003; Koizuka et al., 2003), Rf1 and Rf2 from *sorghum* (*Sorghum bicolor*) (Klein et al., 2005), Rf1a and Rf1b from rice (*Oryza sativa*) for BT-type CMS (Kazama and Toriyama, 2003; Akagi et al., 2004; Komori et al., 2004; Wang et al., 2006), Rf17 (RMS) from rice (*Oryza sativa*) for CW-type CMS (Fujii & Toriyama, 2009), Rf1 & Rf2 from monkey flower (*Mimulus guttatus*) (Barr & Fishman, 2010). Rf4 for CMS C-type of maize was recently cloned.

SUMMARY

Disclosed herein includes methods and reagents for detecting and quantifying the zygosity of the Rf4 gene in plants. The methods can employ and the reagents can include primers and oligonucleotide probes configured for a multiplex, real-time quantitative PCR (qPCR) assay.

In an embodiment, the present method can detect and quantify the zygosity of the Rf4 gene in corn plants in a single reaction. The method can employ primers and oligonucleotide probes that are specific and can distinguish between Rf4 alleles.

In an embodiment, a method for determining zygosity of an Rf4 gene in a corn plant includes: a) performing a first PCR assay using a first probe, a first forward primer, and a first reverse primer on a polynucleotide sample from a corn plant; b) performing a second PCR assay using a second probe, a second forward primer, and a second reverse primer on the polynucleotide sample from a corn plant; c) quantifying the first and second probes; and d) comparing the quantified first and second probes to determine zygosity. In an embodiment, the probes are detectably labeled. In an embodiment, the primers and probes are specific for the Rf4 gene in a corn plant. In an embodiment, a forward primer specific for the Rf4 gene comprises SEQ ID NO:1, SEQ ID NO:11, or SEQ ID NO:15. In an embodiment, a reverse primer specific for the Rf4 gene comprises SEQ ID NO:2, SEQ ID NO:14, or SEQ ID NO:18. In an embodiment, a probe specific for the Rf4 gene comprises SEQ ID NO:4, SEQ ID NO:13, or SEQ ID NO:17.

DETAILED DESCRIPTION

Definitions

Figure 1A:
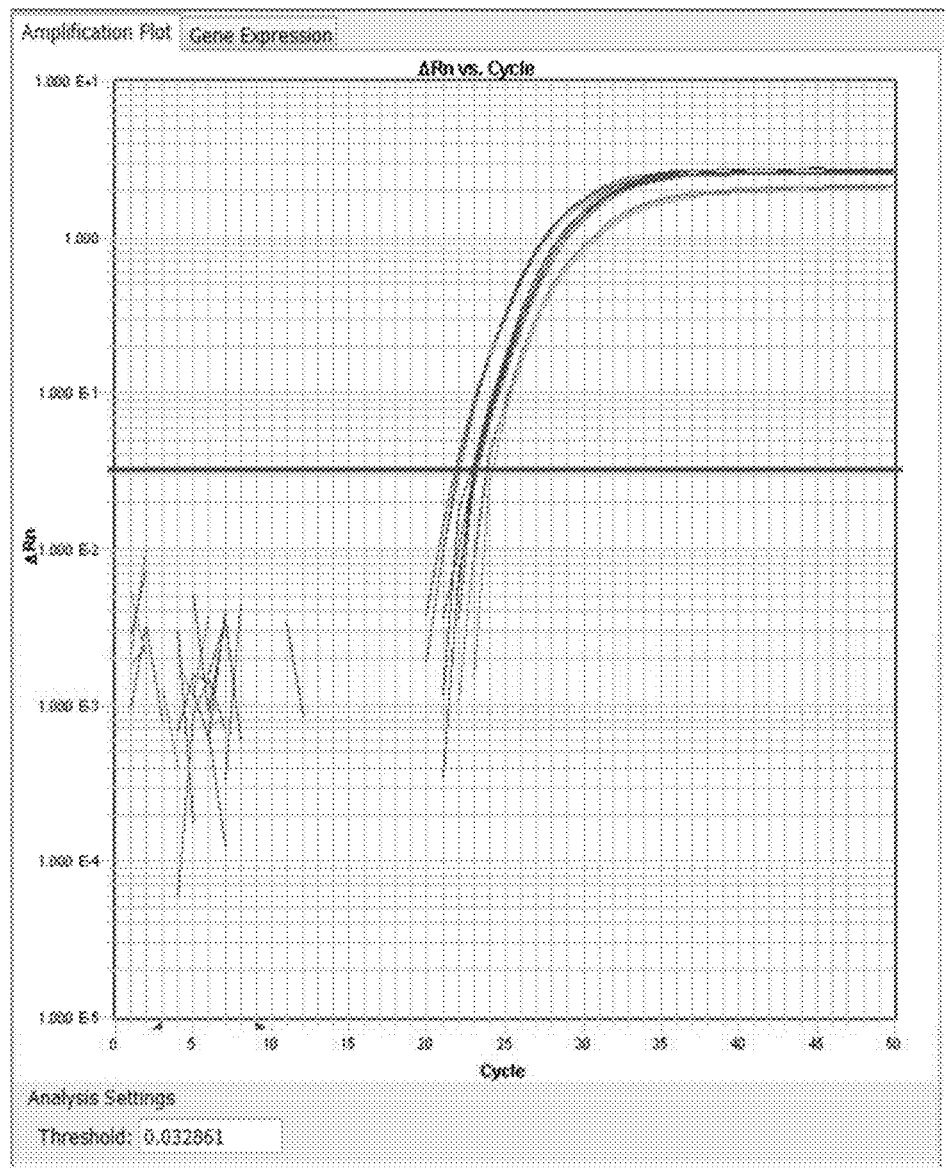
FIG. 1A. Real-time PCR amplification plots with relative fluorescence unit (RFU) are shown for Rf4 with FAM and CMS-C. Exponential amplification phase was observed from cycles 23 to 35 for both Rf4 and CMS-C or non-restorer genes.

The term "sample" refers to a part from any plant species, but preferably is from maize (*Zea mays*). Such can be at the macro or micro level, wherein polynucleotides and/or polypeptides can be extracted.

The term "plant" includes reference to whole plants, plant parts, seeds, plant cells, and progeny of same. Plant parts can include, but are not limited to, leaves, pollen, embryos, cotyledons, hypocotyls, meristematic cells, roots, root tips, anthers, flowers, stems, and pods.

The term "corn" refers to *Zea mays* or maize and includes all plant varieties that can be bred with corn, including wild maize species.

As used herein, "buffer" refers to a buffered solution that resists changes in pH by the action of its acid-base conjugate components. Buffers may optionally comprise a salt such as $MgCl_2$, $MnCl_2$, or the like. Buffers may also optionally comprise other constituents to improve the efficiency of reverse transcription or amplification.

The term "breeding introgression" refers to the movement of a gene or genes through sexual crossing, usually by pollen, from a plant which is intended to be the donor for the formation of seed.

The term "allele" refers to an alternative form of a gene, whereby two genes can differ in DNA sequences. Such differences may result from at least one mutation (e.g., deletion, insertion, and/or substitution) in the nucleic acid sequence. Alleles may result in modified mRNAs or polypeptides whose structure or function may or may not be modified. Any given gene may have none, one, or many allelic forms. Each of these types of changes may occur alone, or in combination with the others, one or more times in a given sequence.

The term "zygosity" refers to the similarity of alleles for a gene or trait in an organism (e.g., a plant). If both alleles are the same, the organism is homozygous for the allele. If the two alleles are different, the organism is heterozygous for the gene or trait. If one allele is not present, the organism is hemizygous. If both alleles are not present, the organism is nullizygous.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin).

The term "oligonucleotide" refers to a single-stranded nucleic acid including at least between two and about 100 natural or modified nucleotides or a mixture thereof. The oligonucleotide can be derived from a natural nucleic acid or produced by chemical or enzymatic synthesis.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label.

"Polypeptide" refers to a peptide or protein containing two or more amino acids linked by peptide bonds, and includes peptides, oligimers, proteins, and the like. Polypeptides can contain natural, modified, or synthetic amino acids. Polypeptides can also be modified naturally, such as by post-translational processing, or chemically, such as amidation, acylation, cross-linking, and the like.

"Polymerase chain reaction" or "PCR" refers to a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51:263 (1987); Erlich, ed., PCR Technology, (Stockton Press, NY, 1989).

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

The term "probe" refers to an oligonucleotide that hybridizes to a target sequence. In the TaqMan® or TaqMan®-style assay procedure, the probe hybridizes to a portion of the target situated between the annealing site of the two primers. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probes 3' end. A probe including a fluorophore may also further include a quencher, e.g., Black Hole Quencher™, Iowa Black™, etc. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides.

The terms "specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions. Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{\hat{}}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) Molecular Cloning: A Laboratory Manual, $2^{nd}$ ed., vol. 1-3, Cold Spring Harbor Laboratory Press, Cold Spring Harbor, N.Y., 1989, chapters 9 and 11; and Hames and Higgins (eds.) Nucleic Acid Hybridization, IRL Press, Oxford, 1985. Further detailed instruction and guidance with regard to the hybridization of nucleic acids may be found, for example, in Tijssen, "Overview of principles of hybridization and the strategy of nucleic acid probe assays," in Laboratory Techniques in Biochemistry and Molecular Biolofiy-Hybridization with Nucleic Acid Probes, Part I, Chapter 2, Elsevier, NY, 1993; and Ausubel et ah, Eds., Current Protocols in Molecular Biology, Chapter 2, Greene Publishing and Wiley-Interscience, NY, 1995.

The term "quenching" refers to a decrease in fluorescence of a fluorescent detectable label caused by energy transfer associated with a quencher moiety, regardless of the mechanism.

The term "reaction mixture" or "PCR reaction mixture" or "master mix" or "master mixture" refers to an aqueous solution of constituents in a PCR or RT-PCR reaction that can be constant across different reactions. An exemplary RT-PCR reaction mixture includes buffer, a mixture of deoxyribonucleoside triphosphates, reverse transcriptase, primers, probes, and DNA polymerase. Generally, template RNA or DNA is the variable in a PCR or RT-PCR reaction.

Rf4 Gene

The use of the fertility restorer gene (Rf) with the cytoplasmic male sterility has been shown to simplify seed production programs and reduce the overall costs by totally eliminating manual and machine detasseling. The restoration gene Rf4 for CMS-C type cytoplasm was previously mapped. The candidate gene Rf4-bHLH was identified, which encoded a basic-Helix-Loop-Helix (bHLH) transcription factor. A 3.2-kb genome DNA fragment was cloned that contained the entire coding region of the Rf4-bHLH gene plus a 1.1 kb 5' UTR/promoter and a 0.75 kb 3' UTR/terminator from a CMS-C line (non-restorer), inbred line (non-CMS) and three restorer lines. Based on nucleotide changes within Rf4 gene between restorer and non-restorer lines, an endpoint TaqMan® PCR assay was developed for Rf4 zygosity test. The assay was validated with an F2 mapping population which contained 500 individuals. This assay enables a large scale screening of maize germplasms in breeding programs for Rf4 restoration gene in a high throughput format. The development of this assay makes it much easier and cheaper to use the CMS-C/Rf4 system for hybrid corn seed production.

Quantitative PCR

Quantitative PCR (qPCR) allows automated quantification of reaction product for each sample per cycle. Commonly used instrumentation and software products perform the quantification calculations automatically. The quantification has a broad $10^7$-fold dynamic range that is possible, but usually, the dynamic range is closer to 2-3 logs. Current instrumentation technology, e.g., Cepheid's Smart Cycler®, allows the simultaneous detection and quantification of fluorescent signals in up to four different channels in real-time. In addition, the latest generation of thermal cyclers is designed to maximize dye excitation providing a more accurate means of detecting fluorescence. Thus, multiple amplification products can be assessed in the same reaction mixture and quantified more accurately ("multiplex PCR" which refers to simultaneous amplification of many targets of interest in one reaction by using more than one pair of primers). Further, each reaction site can be programmed independently, thereby starting the reaction independent of other reactions. Thus, samples can be evaluated as needed and do not have to wait for the completion of a programmed reaction already in progress. Therefore, this new technology now allows for the detection and quantification of multiple targets in a single sample in real-time There are different probe systems for qPCR (e.g., Molecular Beacons (Sigma-Genosys, Inc., The Woodlands, Tex.), Scorpions® (DxS Ltd., Manchester, UK), SYBR® Green (Molecular Probes, Eugene, Oreg.), and TaqMan® (Applied Biosystems, Foster City, Calif.). These systems employ fluorescent labels where the instrumentation detects the fluorescence and the software interprets levels of fluorescence.

TaqMan® utilizes Förster Resonance Energy Transfer (FRET) by coupling a fluorescent label with a quencher moiety. A fluorescent label is covalently bound to the 5' end of an oligonucleotide probe, while the 3' end has a quencher moiety attached. These oligonucleotide probes are site specific to hybridize to the amplified product. Preferably, the oligonucleotide probes are designed to hybridize to a central region of the amplified product. For TaqMan® assays, the 5'-nuclease activity of the DNA polymerase cleaves the probe during the replication cycle. Due to the cleavage of the probe, the quencher moiety is no longer coupled to the fluorescence label and cannot quench fluorescence. Fluorescence thus represents replicating DNA.

Quantification of PCR Results

Standard Curve. Nucleic acids can be used to establish a standard curve. These methods are well known and include internal controls, double stranded DNA, a cDNA expressing a target gene, or an in vitro generated single stranded DNA. Methods may vary according to the nucleic acid chosen to serve as the standard to establish a standard curve.

Comparative Cycle Threshold. The comparative cycle threshold (Ct) method, also known as the $2^{-\Delta\Delta Ct}$ method, is also used to quantify DNA levels. The Ct method compares a test reaction with a control or calibrator sample. The Ct values of both the control/calibrator sample and the test sample are normalized. In an embodiment of the invention, the Ct values were normalized to an arbitrary cutoff, 20-22. In another embodiment, the Ct values were normalized to within 1 Ct value of a negative control (a sample with no inhibition). This allows for the sensitivity of the assay and proper dynamic range.

The Ct method can also be described by the $\Delta\Delta$Ct formula; $\Delta\Delta Ct = \Delta Ct_{test\ sample} - \Delta Ct_{reference\ sample}$. The amplification efficiencies of the test sample and the reference sample must be about the same for the formula to operate. Amplification efficiencies can be determined by a comparison of the samples with template dilution. The amplification efficiency is about the same when a plot of cDNA dilution versus $\Delta$Ct approximates zero.

End-Point Zygosity Assay

An end-point PCR assay for testing Rf4 zygosity in a high throughput way has been developed. This assay enables large scale and high throughput screening of maize germplasms with the Rf4 restoration gene. This assay will also increase the scale of using a CMS-C/Rf4 system for hybrid corn seed production.

In an embodiment, a method for determining the zygosity of the Rf4 gene in a corn plant includes a PCR assay. Such a PCR assay can be quantitative and/or real-time and/or in a multiplex format. In an embodiment, a method employs TaqMan®-style probes (dual-labeled probes to fluoresce upon 5'→3' exonuclease activity). In an embodiment, a method employs TaqMan®-style probes and oligonucleotides that selectively hybridize to the Rf4 gene. In an embodiment, the Rf4 gene probes can be coupled to a detectable label (e.g., 6-carboxyfluorescein) at the 5' end of the oligonucleotide. In an embodiment, the oligonucleotide can also be coupled to a quencher moiety at the 3' end. An example of a quencher moiety for the Rf4 gene probes is Black Hole Quencher™ (Biosearch Technologies, Novato, Calif.). Suitable instrumentation will thereby detect the fluorescence produced from the cleavage of the oligonucleotide probe by the nuclease activity of the DNA polymerase during replication. Analysis software then determines the quantity of amplification product based upon the fluorescence data.

In an embodiment, a method for determining zygosity of an Rf4 gene in a corn plant includes a) performing a first PCR assay using a first probe, a first forward primer, and a first reverse primer on a polynucleotide sample from a corn plant; b) performing a second PCR assay using a second probe, a second forward primer, and a second reverse primer on the polynucleotide sample from a corn plant; c) quantifying the first and second probes; and d) comparing the quantified first and second probes to determine zygosity. In an embodiment, the probes are detectably labeled. In an embodiment, the primers and probes are specific for the Rf4 gene in a corn plant. In an embodiment, a forward primer specific for the Rf4 gene comprises SEQ ID NO:1, 11, or 15. In an embodiment, a reverse primer specific for the Rf4 gene comprises SEQ ID NO:2, 14, or 18. In an embodiment, a probe specific for the Rf4 gene comprises SEQ ID NO:4, 13, or 17.

In an embodiment, a PCR assay method can include loading a PCR reaction mixture in a PCR assay tube, wherein the PCR reaction mixture comprises a polymerase with 5' to 3' nuclease activity, deoxynucleotides, a buffer, a first and a second forward primer, a first and a second reverse primer, a first and a second probe, and a polynucleotide sample, and wherein the first probe and the second probe comprise fluorescent dyes with distinguishable excitation/emission spectra; and performing an amplification step(s) under amplification conditions such that the 5' to 3' nuclease activity of the polymerase cleaves the first and second probes, thereby releasing fluorescent dyes comprising distinguishable excitation/emission spectra.

In another embodiment, a PCR assay method to determine the zygosity of the Rf4 gene includes loading a PCR reaction mixture in a PCR assay tube, wherein the PCR reaction mixture comprises a polymerase with 5' to 3' nuclease activity, deoxynucleotides, a buffer, a first and/or a second forward primer, a first and/or a second reverse primer, a first and/or a second probe, and a polynucleotide sample; and performing an amplification step(s) under conditions such that the 5' to 3' nuclease activity of the polymerase cleaves the first or second probe, thereby releasing fluorescent dyes comprising distinguishable excitation/emission spectra.

In some embodiments, a label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a Bodipy® dye (e.g., FL, 530/550, TR, TMR, etc.), an Alexa Fluor® dye (e.g., 488, 532, 546, 568, 594, 555, 653, 647, 660, 680, etc.), a dichlororhodamine dye, an energy transfer dye (e.g., Bigdye®. v 1 dyes, Bigdye® v 2 dyes, Bigdye® v 3 dyes, etc.), Lucifer dyes (e.g., Lucifer yellow, etc.), Cascade Blue®, Oregon Green®, and the like. Fluorescent dyes can be distinguished and measured during amplification by their emitted excitation and/or emission spectra.

Examples of quenchers include, but are not limited to, Black Hole Quencher™ 1 (BHQ1; Biosearch Technologies, Novato, Calif.), Iowa Black™ (Integrated DNA Technologies), Dabcyl, QSY-7, AbsoluteQuencher, Eclipse®, and Minor Groove Binder (MGB) quencher (Nanogen Inc., San Diego, Calif.).

EXAMPLES

Due to the practical importance of cytoplasmic male sterility and pollen fertility restoration in maize hybrid seed production and the necessity of determining the restoration function of finished lines in the germplasm pool, a high throughput endpoint TaqMan® PCR based zygosity assay was developed to detect and test the zygosity status at Rf4 gene locus efficiently and specifically.

Materials and Methods

Plant genetic material. Nine maize inbred lines were used to develop an endpoint TaqMan® zygosity assay, including three Rf4 fertility restoration lines, three non-restoration lines for CMS C-type, two CMS C-type lines, and one non-restorer and non-CMS-C line. Seeds and/or leaf tissues were sampled for genomic DNA extraction. After the genomic DNA was extracted, the DNA from an Rf4 fertility restoration line was mixed in equal parts with the DNA from a non-restoration CMS C-type line.

One F2 mapping population from the cross of an Rf4 fertility restoration line was mixed in equal parts with the DNA from a non-restoration CMS C-type line resulted in the production with 500 individual plant lines. Samples from this cross were used to validate the endpoint TaqMan® zygosity assay. This population was created in Mexico winter nursery in the end of 2009. Leaf tissues were sampled for DNA extraction.

DNA extraction from seeds. Needle-nosed pliers were used to pull the embryo out of a corn kernel and put into a 1.2 mL sample tube (8 kernels from each line). The pliers were wiped clean in-between kernels. One tungsten alloy bead (~⅛ inch diameter) was added to each tube. Using a Qiagen™ DNA isolation kit, 350 µl of 65° C. AP1 working solution containing 1 µL RNase and 1 µL Reagent DX was added to each tube. Then each tube was capped and ground at 1,500 strokes per minute in an SPEX 2000 Geno/Grinder® (SPEX SamplePrep LLC, Metuchen, N.J.). Subsequently, each tube was spun for 10 seconds at 1500 RPM to remove liquid from the caps. The caps were removed, and 114 µL of AP2 was added. The tubes were capped again and hand-shaken for 15 seconds. Samples were incubated for 10 minutes at −20° C. The samples were centrifuged at 6,000 RPM for 5 minutes. Then each tube was uncapped and 360 µL of supernatant was transferred to tubes containing 540 µL of AP3/E (200 proof ethanol already added to AP3/E). The tubes were capped and hand-shaken for 15 seconds. Then the tubes were centrifuged for 10 seconds at 1500 RPM to remove liquid from the caps. 900 µL was transferred to a DNeasy® filter plate (Qiagen, Valencia, Calif.). The filter plates were centrifuged on an S-Block for 4 minutes at 6000 RPM. Flow-through was poured out from the S-Block and 800 µL of AW (wash buffer—200 proof ethanol already added to AW) was added to each well of the filter plate. The filter plates were centrifuged on an S-Block for 4 minutes at 6000 RPM. 200 µL of 200 proof ethanol were added to each well and centrifuged on the S-Block for 1 minute. The filter plates were placed onto a clean, dry S-block and centrifuged for 15 minutes to dry filters. The filter plates were then placed onto a clean rack of tubes in correct orientation. 100 µL of AE was added to each well twice. Each time, the AE was incubated for 1 minute at room temperature and centrifuged for 2 minutes at 6000 RPM. The filter plates were removed and tubes capped that contained DNA. The extracted DNA was stored at 4° C.

DNA extraction from leaf. Leaf punches (8/plant) were collected from one-month old seedlings, and DNA was extracted using a Biocel® 1800 (Agilent Inc., Santa Clara, Calif.). Specifically, one tungsten alloy bead (~⅛ inch diameter) was added to each tube. Then 300 µL of RLT Lysis Buffer was added to each tube. The tubes were capped and ground for 6 minutes at 1500 strokes per minute in a SPEX 2000 Geno/Grinder® (SPEX SamplePrep LLC). Then the samples were centrifuged 6000 RPM for 5 minutes. The tubes were uncapped.

The following steps were then performed using a Biocel® 1800. 200 µL of supernatant was transferred to a 1.1 mL square well round bottom assay plate containing 10 µL MagAttract® Suspension G Bead (Qiagen) and incubated for 2 minutes. Each well was shaken at 1200 RPM for 40 seconds and then incubated for 2 minutes. The assay plates were placed onto a magnet shelf and the beads were allowed to separate for 40 seconds. Supernatant was then removed. The first time washing, 190 µL RPW wash buffer (premixed RNase® and isopropanol to RPW) was addend and shaken at 1200 RPM for 40 seconds. The assay plate was again placed onto a magnet shelf and the beads were allowed to separate for 20 seconds. The supernatant was removed. The second time washing, 190 µL of 100% ethanol wash buffer was added and shaken at 1200 RPM for 40 seconds. The assay plate was again placed onto a magnet shelf, and the beads were allowed to separate for 20 seconds. The third time washing, 190 µL of 100% ethanol wash buffer was added and shaken at 1200 RPM for 40 seconds. The assay plates were placed onto a magnet shelf and the beads were allowed to separate for 20 seconds. The supernatant was removed, and the plate incubated for 5 minutes at room temperature. 100 µL of AE elution buffer was added and shaken for 2 minutes. The assay plates were placed onto a magnet shelf and the beads were allowed to separate for 30 seconds. The supernatant was transferred to clean, sealed plates and DNA was stored at 4° C. DNA was quantified by using PicoGreen® (Molecular Probes Inc., Eugene, Oreg.) and normalized to 10 ng/µL for further application.

TaqMan® PCR assay design and validation. Primer Express® 3.0 (Perkin-Elmer Corp., Foster City, Calif.) was utilized to design TaqMan® assay primers and probes (Table 1). DNA sequences from Rf4 restoration lines, CMS-C lines, non-CMS-C line and corn line B73 were used. Primers CMSCF and CMSCR were designed for both Rf4 and CMS-C/non-restorer. Probes RCMSC and WCMSC were Rf4 specific at two nucleotides (TT) and CMS-C/non-restorer specific at two nucleotides (AC), respectively.

TABLE 1

Sequences of the primers and MGB probes for Rf4 gene specific zygosity assay:

| CMS-C Rf4 TagMan ® primers and probes | Primer name | SEQ ID NO: |
|---|---|---|
| Forward primer: 5'- CAACGGCGTCGAGAAGAAG -3' | CMSCF | 1 |
| Reverse primer: 5'- TAACGTTGGGTATGAGGTGCAT-3' | CMSCR | 2 |
| rf4(non-restorer) probe: 5'- ACCGAGAAGTACACCGC- 3' | WCMSC | 3 |
| Rf4 (restorer) probe: 5'- CACCGAGAAGTTTACGGC- 3' | RCMSC | 4 |

Primers and probes with FAM or VIC and Minor Grove Binding Non Flourescence Quencher I (MGBFQ) dyes were synthesized by Applied Biosystems (Foster City, Calif.), and were dissolved in 1× Tris-EDTA buffer to 100 µM concentration. TaqMan® gene expression master mixes (Applied Biosystems; and Catalog #4370048) were used for all the PCR reactions.

Real time PCR reactions in 10 µL volume were set up according to Table 2 using 384-well plate on 7900HT Fast Real-Time PCR System (Applied Biosystems) starting with 50° C. for 2 minutes, then denaturing at 95° C. for 10 minutes, followed by 50 cycles of 95° C. for 15 seconds, 60° C. for 1 minute. Fluorescence signals were recorded at the end of each cycle.

TABLE 2

Real-Time PCR Components

| Reagents | Working Con. | Required Con. | 1x vol. (µL) |
|---|---|---|---|
| PVP | 0.5% | 0.08% | 1.55 |
| Gene Expression MM | 2X | 1X | 6.55 |
| Primer Mix | 20 µM | 0.5 µM | 0.25 |
| RCMSC_FAMprobe | 20 µM | 0.2 µM | 0.1 |
| WCMSC_VICprobe | 20 µM | 0.2 µM | 0.1 |
| Total Mix Vol. (µL) | — | — | 7 |
| DNA (10 ng/ul) | — | — | 3 |
| Final PCR vol. (µL) | — | — | 10 |

End-point TaqMan® PCR assays in 10 µL volume was also set up according to Table 2 using 384-well plates. ABI GeneAmp® PCR System 9700 (Applied Biosystems, Foster City, Calif.) was used for amplification starting with 50° C. for 2 minutes, then denaturing at 95° C. for 15 minutes, followed by 40 cycles of 92° C. for 15 seconds and 60° C. for 1 minute. PCR products were measured using Synergy GenS Microplate Reader (BioTek, Winooski, Vt.) and Kraken KLIMS system (KBioscience, England). The instrument settings of recommended wavelengths for reading the PCR results are listed in Table 3.

TABLE 3

Instrument settings with recommended wavelengths for reading the PCR products:

| Dye | Excitation (nm) | Emission (nm) |
|---|---|---|
| FAM (Rf4) | 485 | 535 |
| VIC (CMS-C or non-restorer) | 485 | 560 |

Data analysis. For real-time PCR, the SDS RQ Manager Software performed analyses of relative quantitation data generated by the Applied Biosystems 7900HT Fast Real-Time PCR System. This software displays the amplification plot data in a logarithmic plot of baseline-corrected normalized reporter signal vs. cycle number. The plot displays the amplification curve for each cell selected within the plate grid.

Following the completion of the endpoint TaqMan® PCR and fluorescence reading, the raw fluorescence intensity data directly from the plate reader were analyzed in the KLIMS system. A graph with RFU (relative fluorescence unit) of FAM as x-axis and VIC as y-axis were generated. Determinations of zygosity were made based on the cluster separation in a cluster view.

Results and Discussion

Maize CMS-C Rf4 sequence. High quality Rf4 gene sequences were obtained through cloning and sequencing from six lines (three Rf4 restoration lines: SEQ ID NO:8, SEQ ID NO:10 and SEQ ID NO:9; one CMS-C line: SEQ ID NO:6; one non-CMS-C line: SEQ ID NO:7; and, the B73 line: SEQ ID NO:5). Sequences were analyzed and aligned using Sequencher® 4.8 (Gene Codes Corp., Ann Arbor, Mich.). Rf4-bHLH genomic sequence alignment is depicted below.

```
                                                                  SEQ ID NO. 5
  (1) GGCAAGCTAATGGGGTACATATGGAAGGAGGAAACCAAGTCGATCGTCGTCGTAGCATGTCGGTGTGGGTACTACA
      CTACACACACATATACATGGGCAA

SEQ ID NO: 6
  (1) GGCAAGCTAATGGGGTACATATGGAAGGAGGAAACCAAGTCGATCGTCGTCGTAGCATGTCGGTGTGGGTACTACA
      CTACACACACATATACATGGGCAA

SEQ ID NO: 7
  (1) GGCAAGCTAATGGGGTACATATGGAAGGAGGAAACCAAGTCGATCGTCGTCGTAGCATGTCGGTGTGGGTACTACA
      CTACACACACATATACATGGGCAA

SEQ ID NO: 8
  (1) GGCAAGCTAATGGGGTACATATGGAAGGAGGAAACCAAGTCGATCGTCGTCGTAGCATGTCGGTGTGGGTACTACA
      CTACACACACATATACATGGGCAA

SEQ ID NO: 9
  (1) GGCAAGCTAATGGGGTACATATGGAAGGAGGAAACCAAGTCGATCGTCGTCGTAGCATGTCGGTGTGGGTACTACA
      CTACACACACATATACATGGGCAA

SEQ ID NO: 10
  (1) GGCAAGCTAATGGGGTACATATGGAAGGAGGAAACCAAGTCGATCGTCGTCGTAGCATGTCGGTGTGGGTACTACA
      CTACACACACATATACATGGGCAA (101) CGCAAGGCCACCTTTCTGAATCCTGCATGAGCGTGTACCACTAGAATTGTCAGTGTGTGCGGTGTATGGCAGGTTT
      TTGGTTCGGCAAGTGGGGCCCTCC (101) CGCAAGGCCACCTTTCTGAATCCTGCATGAGCGTGTACCACTAGAATTGTCAGTGTGTGCGGTGTATGGCAGGTTT
      TTGGTTCGGCAAGTGGGGCCCTCC (101) CGCAAGGCCACCTTTCTGAATCCTGCATGAGCGTGTACCACTAGAATTGTCAGTGTGTGCGGTGTATGGCAGGTTT
      TTGGTTCGGCAAGTGGGGCCCTCC (101) CGCAAGGCCACCTTTCTGAATCCTGCATGAGCGTGTACCACTAGAATTGTCAGTGTGTGCGGTGTATGGCAGGTTT
      TTGGTTCGGCAAGTGGGGCCCTCC (101) CGCAAGGCCACCTTTCTGAATCCTGCATGAGCGTGTACCACTAGAATTGTCAGTGTGTGCGGTGTATGGCAGGTTT
      TTGGTTCGGCAAGTGGGGCCCTCC (101) CGCAAGGCCACCTTTCTGAATCCTGCATGAGCGTGTACCACTAGAATTGTCAGTGTGTGCGGTGTATGGCAGGTTT
      TTGGTTCGGCAAGTGGGGCCCTCC (201) GGGGAGGAATCTCAGTAACAAACCGCTCTTCTGAAAAGGTCAGCCATCCCCGGTCCGGTCCGGTGATGTCGTCGCT
      GTCGCTCTGCTAGCTTGCTGCCGA (201) GGGGAGGAATCTCAGTAACAAACCGCTCTTCTGAAAAGGTCAGCCATCCCCGGTCCGGTCCGGTGATGTCGTCGCT
      GTCGCTCTGCTAGCTTGCTGCCGA (201) GGGGAGGAATCTCAGTAACAAACCGCTCTTCTGAAAAGGTCAGCCATCCCCGGTCCGGTCCGGTGATGTCGTCGCT
      GTCGCTCTGCTAGCTTGCTGCCGA (201) GGGGAGGAATCTCAGTAACAAACCGCTCTTCTGAAAAGGTCAGCCATCCCCGGTCCGGTCCGGTGATGTCGTCGCT
      GTCGCTCTGCTAGCTTGCTGCCGA (201) GGGGAGGAATCTCAGTAACAAACCGCTCTTCTGAAAAGGTCAGCCATCCCCGGTCCGGTCCGGTGATGTCGTCGCT
      GTCGCTCTGCTAGCTTGCTGCCGA (201) GGGGAGGAATCTCAGTAACAAACCGCTCTTCTGAAAAGGTCAGCCATCCCCGGTCCGGTCCGGTGATGTCGTCGCT
      GTCGCTCTGCTAGCTTGCTGCCGA (301) TCCCCCCCCCCCCCCCCCCCCTTCTTCTCTCTACCCCTCCCTCCACCTCATAAATACTTAGTTTAATAACCTTGCA
      CTGCCGCAGTAGCCCTTAACTGCT (301) TCCCCCCCCCCCCCCCCCCCCTTCTTCTCTCTACCCCTCCCTCCACCTCATAAATACTTAGTTTAATAACCTTGCA
      CTGCCGCAGTAGCCCTTAACTGCT (301) TCCCCCCCCC-----------TTCTTCTCTCTACCCCTCCCTCCACCTCATAAATACTTAGTTTAATAACCTTGCA
      CTGCCGCAGTAGCCCTTAACTGCT (301) TCCCCCCCCCCCCCCCCCCCCTTCTTCTCTCTACCCCTCCCTCCACCTCATAAATACTTAGTTTAATAACCTTGCA
      CTGCCGCAGTAGCCCTTAACTGCT (301) TCCCCCCCCCCCCCCCCCCCCTTCTTCTCTCTACCCCTCCCTCCACCTCATAAATACTTAGTTTAATAACCTTGCA
      CTGCCGCAGTAGCCCTTAACTGCT (301) TCCCCCCCCCCCCCCCCCCCCTTCTTCTCTCTACCCCTCCCTCCACCTCATAAATACTTAGTTTAATAACCTTGCA
      CTGCCGCAGTAGCCCTTAACTGCT (401) GCTATCTATCTCTTTTCTGAAGGAAAAAAAAGGTTTGATACTCCTCTACCTAGCTAGTCCTGCATGCCGCTAATGT
      GCGTCTTGCCTGTTTATTTGTTCT
```

```
(401) GCTATCTATCTCTTTTCTGAAGGAAAAAAAAGGTTTGATACTCCTCTACCTAGCTAGTCCTGCATGCCGCTAATGT
      GCGTCTTGCCTGTTTATTTGTTCT (390) GCTATCTATCTCTTTTCTGAAGGAAAAAAAAGGTTTGATACTCCTCTACCTAGCTAGTCCTGCATGCCGCTAATGT
      GCGTCTTGCCTGTTTATTTGTTCT (401) GCTATCTATCTCTTTTCTGAAGGAAAAAAAAGGTTTGATACTCCTCTACCTAGCTAGTCCTGCATGCCGCTAATGT
      GCGTCTTGCCTGTTTATTTGTTCT (401) GCTATCTATCTCTTTTCTGAAGGAAAAAAAAGGTTTGATACTCCTCTACCTAGCTAGTCCTGCATGCCGCTAATGT
      GCGTCTTGCCTGTTTATTTGTTCT (401) GCTATCTATCTCTTTTCTGAAGGAAAAAAAAGGTTTGATACTCCTCTACCTAGCTAGTCCTGCATGCCGCTAATGT
      GCGTCTTGCCTGTTTATTTGTTCT

DAS-CMS21
(501) TAATAAGGGCTGCCTATCTATTATATTTTGCACCTGTTTTGCTGTGTTCTTGGTAACTAGCTTAATTCCTTCGCCT
      ACAATCGTCAAATCCCCCCCATCA (501) TAATAAGGGCTGCCTATCTATTATATTTTGCACCTGTTTTGCTGTGTTCTTGGTAACTAGCTTAATTCCTTCGCCT
      ACAATCGTCAAATCCCCCCCATCA (490) TAATAAGGGCTGCCTATCTATTATATTTTGCACCTGTTTTGCTGTGTTCTTGGTAACTAGCTTAATTCCTTTGCCT
      ACAATCGTCAAATCCCCCCCATCA (501) TAATAAGGGCTGCCTATCTATTATATTTTGCACCTGTTTTGCTGTGTTCTTGGTAACTAGCTTAATTCCTTTGCCT
      ACAATCGTCAAATCCCCCCCATCA (501) TAATAAGGGCTGCCTATCTATTATATTTTGCACCTGTTTTGCTGTGTTCTTGGTAACTAGCTTAATTCCTTTGCCT
      ACAATCGTCAAATCCCCCCCATCA (501) TAATAAGGGCTGCCTATCTATTATATTTTGCACCTGTTTTGCTGTGTTCTTGGTAACTAGCTTAATTCCTTTGCCT
      ACAATCGTCAAATCCCCCCCATCA (601) TCAGTCAGATGAACTTTTGATCGAATTGAAGTTGTTCTTCTAATTCGGCCCCAGCAGCGCCCATGCATCTGGTTTT
      ATTTGCTTTCTGTTGGGTATAATA (601) TCAGTCAGATGAACTTTTGATCGAATTGAAGTTGTTCTTCTAATTCGGCCCCAGCAGCGCCCATGCATCTGGTTTT
      ATTTGCTTTCTGTTGGGTATAATA (590) TCAGTCAGATGAACTTTTGATCGAATTGAAGTTGTTCTTCTAATTCGGCCCCAGCAGCGCCCATGCATCTGGTTTT
      ATTTGCTTTCTGTTGGGTATAATA (601) TCAGTCAGATGAACTTTTGATCGAATTGAAGTTGTTCTTCTAATTCGGCCCCAGCAGCGCCCATGCATCTGGTTTT
      ATTTGCTTTCTGTTGGGTATAATA (601) TCAGTCAGATGAACTTTTGATCGAATTGAAGTTGTTCTTCTAATTCGGCCCCAGCAGCGCCCATGCATCTGGTTTT
      ATTTGCTTTCTGTTGGGTATAATA (601) TCAGTCAGATGAACTTTTGATCGAATTGAAGTTGTTCTTCTAATTCGGCCCCAGCAGCGCCCATGCATCTGGTTTT
      ATTTGCTTTCTGTTGGGTATAATA (701) TGCAAGACCTTTTGTTGCTAGGGCAAGGCTGCAACCACATGCGTGTACTGAACTCATGATGTAACTCATCCTTTTT
      GTTTGCTCACAGAATCACTACTCT (701) TGCAAGACCTTTTGTTGCTAGGGCAAGGCTGCAACCACATGCGTGTACTGAACTCATGATGTAACTCATCCTTTTT
      GTTTGCTCACAGAATCACTACTCT (690) TGCAAGACCTTTTGTTGCTAGGGCAAGGCTGCAACCACATGCGTGTACTGAACTCATGATGTAACTCATCCTTTTT
      GTTTGCTCACAGAATCACTACTCT (701) TGCAAGACCTTTTGTTGCTAGGGCAAGGCTGCAACCACATGCGTGTACTGAACTCATGATGTAACTCATCCTTTTT
      GTTTGCTCACAGAATCACTACTCT (701) TGCAAGACCTTTTGTTGCTAGGGCAAGGCTGCAACCACATGCGTGTACTGAACTCATGATGTAACTCATCCTTTTT
      GTTTGCTCACAGAATCACTACTCT (701) TGCAAGACCTTTTGTTGCTAGGGCAAGGCTGCAACCACATGCGTGTACTGAACTCATGATGTAACTCATCCTTTTT
      GTTTGCTCACAGAATCACTACTCT (801) ACTGCACTTCCTTTTCATCCGATCCGCAATCTTTTTTTCTTTTACATGCTTTAGTTTTCTCTCTTTCTTGATTAC
      AAACATGATTACTGGAACTTTCTT (801) ACTGCACTTCCTTTTCATCCGATCCGCAATCTTTTTTTCTTTTACATGCTTTAGTTTTCTCTCTTTCTTGATTAC
      AAACATGATTACTGGAACTTTCTT (790) ACTGCACTTCCTTTTCATCCGATCCGCAATCTTTTTTTCTTTTACATGCTTTAGTTTTCTCTCTTTCTTGATTAC
      AAACATGATTACTGGAACTTTCTT (801) ACTGCACTTCCTTTTCATCCGATCCGCAATCTTTTTTTCTTTTACATGCTTTAGTTTTCTCTCTTTCTTGATTAC
      AAACATGATTACTGGAACTTTCTT
```

```
-continued (801) ACTGCACTTCCTTTTCATCCGATCCGCAATCTTTTTTTTCTTTTACATGCTTTAGTTTTCTCTCTTTCTTGATTAC
        AAACATGATTACTGGAACTTTCTT (801) ACTGCACTTCCTTTTCATCCGATCCGCAATCTTTTTTTTCTTTTACATGCTTTAGTTTTCTCTCTTTCTTGATTAC
        AAACATGATTACTGGAACTTTCTT (901) AGGCTGCCTTCCCCTTCCTTGGATCTGCTTTAGTTTTCTTTTTTGGGCTACCGCGCGCGGCTTATTTGAGTTTATC
        ACTTGCTGCATATACATAATATAT (901) AGGCTGCCTTCCCCTTCCTTGGATCTGCTTTAGTTTTCTTTTTTGGGCTACCGCGCGCGGCTTATTTGAGTTTATC
        ACTTGCTGCATATACATAATATAT (890) AGGCTGCCTTCCCCTTCCTTGGATCTGCTTTAGTTTTCTTTTTTGGGCTACCGCGCGCGGCTTATTTGAGTTTATC
        ACTTGCTGCATATACATAATATAT (901) AGGCTGCCTTCCCCTTCCTTGGATCTGCTTTAGTTTTCTTTTTTGGGCTACCGCGCGCGGCTTATTTGAGTTTATC
        ACTTGCTGCATATACATAATATAT (901) AGGCTGCCTTCCCCTTCCTTGGATCTGCTTTAGTTTTCTTTTTTGGGCTACCGCGCGCGGCTTATTTGAGTTTATC
        ACTTGCTGCATATACATAATATAT (901) AGGCTGCCTTCCCCTTCCTTGGATCTGCTTTAGTTTTCTTTTTTGGGCTACCGCGCGCGGCTTATTTGAGTTTATC
        ACTTGCTGCATATACATAATATAT (1001) ATATACATGCATGCGATGGCGTTCATGTTACTCAACTACAGATCTGTTTCTGTTCGTGTGTTTCAGTTCAGCGCGC
        AGTTAAGCATAGCAGGACGACCAC (1001) ATATACATGCATGCGATGGCGTTCATGTTACTCAACTACAGATCTGTTTCTGTTCGTGTGTTTCAGTTCAGCGCGC
        AGTTAAGCATAGCAGGACGACCAC (990) ATATACATGCATGCGATGGCGTTCATGTTACTCAACTACAGATCTGTTTCTGTTCGTGTGTTTCAGTTCAGCGCGC
        AGTTAAGCATAGCAGGACGACCAC (1001) ATATACATGCATGCGATGGCGTTCATGTTACTCAACTACAGATCTGTTTCTGTTCGTGTGTTTCAGTTCAGCGCGC
        AGTTAAGCATAGCAGGACGACCAC (1001) ATATACATGCATGCGATGGCGTTCATGTTACTCAACTACAGATCTGTTTCTGTTCGTGTGTTTCAGTTCAGCGCGC
        AGTTAAGCATAGCAGGACGACCAC (1001) ATATACATGCATGCGATGGCGTTCATGTTACTCAACTACAGATCTGTTTCTGTTCGTGTGTTTCAGTTCAGCGCGC
        AGTTAAGCATAGCAGGACGACCAC START
 (1101) GACGATGTATCACCCGCAGTGCGAGCTCCTGACGATGGCGCACGAAACGCCGGACCTGGACGCCGGCCAGCCGCAC
        CTAACCGTCTCCGGCGTCGCCAGC (1101) GACGATGTATCACCCGCAGTGCGAGCTCCTGACGATGGCGCACGAAACGCCGGACCTGGACGCCGGCCAGCCGCAC
        CTAACCGTCTCCGGCGTCGCCAGC (1090) GACGATGTATCACCCGCAGTGCGAGCTCCTGACGATGGCGCACGAAACGCCGGACCTGGACGCCGGCCAGCCGCAC
        CTAACCGTCTCCGGCGTCGCCAGC (1101) GACGATGTATCACCCGCAGTGCGAGCTCCTGACGATGGCGCACGAAACGCCGGACCTGGACGCCGGCCAGCCGCAC
        CTAACCGTCTCCGGCGTCGCCAGC (1101) GACGATGTATCACCCGCAGTGCGAGCTCCTGACGATGGCGCACGAAACGCCGGACCTGGACGCCGGCCAGCCGCAC
        CTAACCGTCTCCGGCGTCGCCAGC (1101) GACGATGTATCACCCGCAGTGCGAGCTCCTGACGATGGCGCACGAAACGCCGGACCTGGACGCCGGCCAGCCGCAC
        CTAACCGTCTCCGGCGTCGCCAGC (1201) ATCCCGGCAGAGCTGAGCTTCCACCTGCTGCACTCGCTCGACGCCGCGGCGGCGGTCAATCCCGTCACGGCGCCGC
        CGCAGTCCACCATCGACTACTTCC (1201) ATCCCGGCAGAGCTGAGCTTCCACCTGCTGCACTCGCTCGACGCCGCGGCGGCGGTCAATCCCGTCACGGCGCCGC
        CGCAGTCCACCATCGACTACTTCC (1190) ATCCCGGCAGAGCTGAGCTTCCACCTGCTGCACTCGCTCGACGCCGCGGCGGCGGTCAATCCCGTCACGGCGCCGC
        CGCAGTCCACCATCGACTACTTCC (1201) ATCCCGGCAGAGCTGAGCTTCCACCTGCTGCACTCGCTCGACGCCGCGGCGGCGGTCAATCCCGTCACGGCGCCGC
        CGCAGTCCACCATCGACTACTTCC (1201) ATCCCGGCAGAGCTGAGCTTCCACCTGCTGCACTCGCTCGACGCCGCGGCGGCGGTCAATCCCGTCACGGCGCCGC
        CGCAGTCCACCATCGACTACTTCC (1201) ATCCCGGCAGAGCTGAGCTTCCACCTGCTGCACTCGCTCGACGCCGCGGCGGCGGTCAATCCCGTCACGGCGCCGC
        CGCAGTCCACCATCGACTACTTCC
```

-continued (1301) TCGGCGGCGCCGATCCCCACCAGCAGGCCATGCAGTACGAGCCGCTGCCGCCCGCCGCGGGCGGCCACCACCAGTA
       CACCATGGACATGTTCCGCGACTA (1301) TCGGCGGCGCCGATCCCCACCAGCAGGCCATGCAGTACGAGCCGCTGCCGCCCGCCGCGGGCGGCCACCACCAGTA
       CACCATGGACATGTTCCGCGACTA (1290) TCGGCGGCGCCGATCCCCACCAGCAGGCCATGCAGTACGAGCCGCTGCCGCCCGCCGCGGGCGGCCACCACCAGTA
       CACCATGGACATGTTCCGCGACTA (1301) TCGGCGGCGCCGATCCCCACCAGCAGGCCATGCAGTACGAGCCGCTGCCGCCCGCCGCGGGCGGCCACCACCAGTA
       CACCATGGACATGTTCCGCGACTA (1301) TCGGCGGCGCCGATCCCCACCAGCAGGCCATGCAGTACGAGCCGCTGCCGCCCGCCGCGGGCGGCCACCACCAGTA
       CACCATGGACATGTTCCGCGACTA (1301) TCGGCGGCGCCGATCCCCACCAGCAGGCCATGCAGTACGAGCCGCTGCCGCCCGCCGCGGGCGGCCACCACCAGTA
       CACCATGGACATGTTCCGCGACTA DAS-CMS22(H/N)
(1401) CTGCGACGGCCACTACCCCACCGCCGAGCCGTACATCCGCGGGACAATGACTGGAGCCCTCGTGTTCGGGGCCACC
       GACGACGACGACTCGGCCGCTGCC (1401) CTGCGACGGCCACTACCCCACCGCCGAGCCGTACATCCGCGGGACAATGACTGGAGCCCTCGTGTTCGGGGCCACC
       GACGACGACGACTCGGCCGCTGCC (1390) CTGCGACGGCCACTACCCCACCGCCGAGCCGTACATCCGCGGGACAATGACTGGAGCCCTCGTGTTCGGGGCCACC
       GACGACGACGACTCGGCCGCTGCC (1401) CTGCGACGGCAACTACCCCACCGCCGAGCCGTACATCCGCGGGACAATGACTGGAGCCCTCGTGTTCGGGGCCACC
       GACGACGACGACTCGGCCGCTGCC (1401) CTGCGACGGCAACTACCCCACCGCCGAGCCGTACATCCGCGGGACAATGACTGGAGCCCTCGTGTTCGGGGCCACC
       GACGACGACGACTCGGCCGCTGCC (1401) CTGCGACGGCAACTACCCCACCGCCGAGCCGTACATCCGCGGGACAATGACTGGAGCCCTCGTGTTCGGGGCCACC
       GACGACGACGACTCGGCCGCTGCC DAS-CMS23(-/A)
(1500) ---TACATGCCCGGGGGGCACTTTGAGACCTCCCCGCCGCCGCCACGCGCCACCGGCCGCGGCAGGAAGCGGGGCA
       GGGCGCTGGGCGGCGGCTTCCATG (1500) ---TACATGCCCGGGGGGCACTTTGAGACCTCCCCGCCGCCGCCACGCGCCACCGGCCGCGGCAGGAAGCGGGGCA
       GGGCGCTGGGCGGCGGCTTCCATG (1489) ---TACATGCCCGGGGGGCACTTTGAGACCTCCCCGCCGCCGCCACGCGCCACCGGCCGCGGCAGGAAGCGGGGCA
       GGGCGCTGGGCGGCGGCTTCCATG (1501) GCCTACATGCCCGGGGGGCACTTTGAGACCTCCCCGCCGCCGCCACGCGCCACCGGCCGCGGCAGGAAGCGGGGCA
       GGGCGCTGGGCGGCGGCTTCCATG (1501) GCCTACATGCCCGGGGGGCACTTTGAGACCTCCCCGCCGCCGCCACGCGCCACCGGCCGCGGCAGGAAGCGGGGCA
       GGGCGCTGGGCGGCGGCTTCCATG (1501) GCCTACATGCCCGGGGGGCACTTTGAGACCTCCCCGCCGCCGCCACGCGCCACCGGCCGCGGCAGGAAGCGGGGCA
       GGGCGCTGGGCGGCGGCTTCCATG DAS-CMS35(Y/F)  DAS-CMS24
(1598) CTGTGCTGGCCAACGGCGTCGAGAAGAAGGAGAAGCAGCGCCGGCTGCGGCTCACCGAGAAGTACACCGCCCTCAT
              DAS-CMS25
       GCACCTCATACCCAACGTTACAAA (1598) CTGTGCTGGCCAACGGCGTCGAGAAGAAGGAGAAGCAGCGCCGGCTGCGGCTCACCGAGAAGTACACCGCCCTCAT
       GCACCTCATACCCAACGTTACAAA (1587) CTGTGCTGGCCAACGGCGTCGAGAAGAAGGAGAAGCAGCGCCGGCTGCGGCTCACCGAGAAGTACACCGCCCTCAT
       GCACCTCATACCCAACGTTACAAA (1601) CTGTGCTGGCCAACGGCGTCGAGAAGAAGGAGAAGCAGCGCCGGCTGCGGCTCACCGAGAAGTTTACGGCCCTCAT
       GCACCTCATACCCAACGTTACGAA (1601) CTGTGCTGGCCAACGGCGTCGAGAAGAAGGAGAAGCAGCGCCGGCTGCGGCTCACCGAGAAGTTTACGGCCCTCAT
       GCACCTCATACCCAACGTTACGAA (1601) CTGTGCTGGCCAACGGCGTCGAGAAGAAGGAGAAGCAGCGCCGGCTGCGGCTCACCGAGAAGTTTACGGCCCTCAT
       GCACCTCATACCCAACGTTACGAA DAS-CMS26
(1698) GGTCGTAC------------------CAAATCCTCCTCTTATGTTCGTC---CATCGTTTC AAATTAAGTTAAAA
       AATTAATTCACGGTTCTTGTTGTT

```
(1698) GGTCGTAC------------------CAAATCCTCCTCTTATGTTCGTC---CATCGTTTCAAATTAAGTTAAAA
       AATTAATTCACGGTTCTTGTTGTT (1687) GGTCGTAC------------------CAAATCCTCCTCTTATGTTCGTC---CATCGTTTGAAATTAAGTTAAAA
       AATTAATTCACGGTTCTTGTTGTT (1701) GGTCGTACGGCGTACTTGCGCGCGGACCAAATCCTCCTCTTATGTTCGTCGTCCATCGTCTCAAATTAA-------
       ------TTCACGGTTCTTGTTGTT (1701) GGTCGTACGGCGTACTTGCGCGCGGACCAAATCCTCCTCTTATGTTCGTCGTCCATCGTCTCAAATTAA-------
       ------TTCACGGTTCTTGTTGTT (1701) GGTCGTACGGCGTACTTGCGCGCGGACCAAATCCTCCTCTTATGTTCGTCGTCCATCGTCTCAAATTAA-------
       ------TTCACGGTTCTTGTTGTT

DAS-CMS27
(1776) ---TATTTTTTGCGCACTGCAGACTGATAGGGCGACGGTGATCTCGGACGCGATCGAGTACATCCAGGAGCTGGGG
       AGGACGGTGGAGGAGCTGACGCTG (1776) ---TATTTTTTGCGCACTGCAGACTGATAGGGCGACGGTGATCTCGGACGCGATCGAGTACATCCAGGAGCTGGGG
       AGGACGGTGGAGGAGCTGACGCTG (1765) ---TATTTTTTGCGCACTGCAGACTGATAGGGCGACGGTGATCTCGGACGCGATCGAGTACATCCAGGAGCTGGGG
       AGGACGGTGGAGGAGCTGACGCTG (1788) GTTTATTTTTTGCGCACTGCAGACTGATAGGGCGACGGTGATCTCGGACGCGATCGAGTACATCCAGGAGCTGGGG
       AGGACGGTGGAGGAGCTGACGCTG (1788) GTTTATTTTTTGCGCACTGCAGACTGATAGGGCGACGGTGATCTCGGACGCGATCGAGTACATCCAGGAGCTGGGG
       AGGACGGTGGAGGAGCTGACGCTG (1788) GTTTATTTTTTGCGCACTGCAGACTGATAGGGCGACGGTGATCTCGGACGCGATCGAGTACATCCAGGAGCTGGGG
       AGGACGGTGGAGGAGCTGACGCTG (1873) CTGGTGGAGAAGAAGCGGCGCCGGAGGGAGCTGCAGGGGACGTCGTGGACGCGGCGCCGGCTGCGGTGGTTGCTG
       CCGCCGGTGAGGCGGAGAGCTCGG (1873) CTGGTGGAGAAGAAGCGGCGCCGGAGGGAGCTGCAGGGGACGTCGTGGACGCGGCGCCGGCTGCGGTGGTTGCTG
       CCGCCGGTGAGGCGGAGAGCTCGG (1862) CTGGTGGAGAAGAAGCGGCGCCGGAGGGAGCTGCAGGGGACGTCGTGGACGCGGCGCCGGCTGCGGTGGTTGCTG
       CCGCCGGTGAGGCGGAGAGCTCGG (1888) CTGGTGGAGAAGAAGCGGCGCCGGAGGGAGCTGCAGGGGACGTCGTGGACGCGGCGCCGGCTGCGGTGGTTGCTG
       CCGCCGGTGAGGCGGAGAGCTCGG (1888) CTGGTGGAGAAGAAGCGGCGCCGGAGGGAGCTGCAGGGGACGTCGTGGACGCGGCGCCGGCTGCGGTGGTTGCTG
       CCGCCGGTGAGGCGGAGAGCTCGG (1888) CTGGTGGAGAAGAAGCGGCGCCGGAGGGAGCTGCAGGGGACGTCGTGGACGCGGCGCCGGCTGCGGTGGTTGCTG
       CCGCCGGTGAGGCGGAGAGCTCGG

DAS-CMS28(P/L)
(1973) AGGGCGAGGTGGCTCCTCCGCCGCCGGCCGTGCCGCGGCAGCCGATCCGGAGCACGTACATCCAGCGGCGGAGCAA
       GGACACGTCCGTGGACGTGCGGAT (1973) AGGGCGAGGTGGCTCCTCCGCCGCCGGCCGTGCCGCGGCAGCCGATCCGGAGCACGTACATCCAGCGGCGGAGCAA
       GGACACGTCCGTGGACGTGCGGAT (1962) AGGGCGAGGTGGCTCCTCCGCCGCCGGCCGTGCCGCGGCAGCCGATCCGGAGCACGTACATCCAGCGGCGGAGCAA
       GGACACGTCCGTGGACGTGCGGAT (1988) AGGGCGAGGTGGCTCCTCCGCCGCTGGCCGTGCCGCGGCAGCCGATCCGGAGCACGTACATCCAGCGGCGGAGCAA
       GGACACGTCCGTGGACGTGCGGAT (1988) AGGGCGAGGTGGCTCCTCCGCCGCTGGCCGTGCCGCGGCAGCCGATCCGGAGCACGTACATCCAGCGGCGGAGCAA
       GGACACGTCCGTGGACGTGCGGAT (1988) AGGGCGAGGTGGCTCCTCCGCCGCTGGCCGTGCCGCGGCAGCCGATCCGGAGCACGTACATCCAGCGGCGGAGCAA
       GGACACGTCCGTGGACGTGCGGAT (2073) CGTGGAGGAGGACGTGAACATCAAGCTCACCAAGCGCCGGCGCGACGGGTGCCTCGCAGCCGCGTCGCGCGCGCTG
           DAS-CMS29
           GATGACCTCCGCCTTGACCTCGTC (2073) CGTGGAGGAGGACGTGAACATCAAGCTCACCAAGCGCCGGCGCGACGGGTGCCTCGCAGCCGCGTCGCGCGCGCTG
       GATGACCTCCGCCTTGACCTCGTC (2062) CGTGGAGGAGGACGTGAACATCAAGCTCACCAAGCGCCGGCGCGACGGGTGCCTCGCAGCCGCGTCGCGCGCGCTG
       GATGACCTCCGCCTTGACCTCGTC
```

-continued (2088) CGTGGAGGAGGACGTGAACATCAAGCTCACCAAGCGCCGGCGCGACGGGTGCCTCGCAGCCGCGTCGCGCGCGCTG
GACGACCTCCGCCTTGACCTCGTC (2088) CGTGGAGGAGGACGTGAACATCAAGCTCACCAAGCGCCGGCGCGACGGGTGCCTCGCAGCCGCGTCGCGCGCGCTG
GACGACCTCCGCCTTGACCTCGTC (2088) CGTGGAGGAGGACGTGAACATCAAGCTCACCAAGCGCCGGCGCGACGGGTGCCTCGCAGCCGCGTCGCGCGCGCTG
GACGACCTCCGCCTTGACCTCGTC (2173) CACCTCTCCGGCGGCAAGATCGGTGACTGTCAAATCTACATGTTCAACACCAAGGTACATACGAATACGATACGTA
GCCATTGATCGATCTGTAATTCTG (2173) CACCTCTCCGGCGGCAAGATCGGTGACTGTCAAATCTACATGTTCAACACCAAGGTACATACGAATACGATACGTA
GCCATTGATCGATCTGTAATTCTG (2162) CACCTCTCCGGCGGCAAGATCGGTGACTGTCAAATCTACATGTTCAACACCAAGGTACATACGAATACGATACGTA
GCCATTGATCGATCTGTAATTCTG (2188) CACCTCTCCGGCGGCAAGATCGGTGACTGTCAAATCTACATGTTCAACACCAAGGTACATACGAATACGATACGTA
GCCATTGATCGATCTGTAATTCTG (2188) CACCTCTCCGGCGGCAAGATCGGTGACTGTCAAATCTACATGTTCAACACCAAGGTACATACGAATACGATACGTA
GCCATTGATCGATCTGTAATTCTG (2188) CACCTCTCCGGCGGCAAGATCGGTGACTGTCAAATCTACATGTTCAACACCAAGGTACATACGAATACGATACGTA
GCCATTGATCGATCTGTAATTCTG

```
                   DAS-CMS30
```
(2273) TAGCCTGACGATT---------------CCGAGGTTTCTG--------------------GTGCTAAAAAATGCAT
CTTTTTTTCTCAGATGACAATGCT (2273) TAGCCTGACGATT---------------CCGAGGTTTCTG--------------------GTGCTAAAAAATGCAT
CTTTTTTTCTCAGATGACAATGCT (2262) TAGCCTGACGATT---------------CCGAGGTTTCTG--------------------GTGCTAAAAAATGCAT
CTTTTTTTCTCAGATGACAATGCT (2288) TAGCCTGACGATTTCATGCATTACTTTTCCGAGGTTTCTGTGCTATACTACCTAACCTAGGTGCTAAAAAATGCAC
CTTTTTTTCTCAGATGACAATGCT (2288) TAGCCTGACGATTTCATGCATTACTTTTCCGAGGTTTCTGTGCTATACTACCTAACCTAGGTGCTAAAAAATGCAC
CTTTTTTTCTCAGATGACAATGCT (2288) TAGCCTGACGATTTCATGCATTACTTTTCCGAGGTTTCTGTGCTATACTACCTAACCTAGGTGCTAAAAAATGCAC
CTTTTTTTCTCAGATGACAATGCT (2338) TTCTGTCTTTGTTCACCGCAGATTCACAAGGGGTCTTCAGTGTTTGCGAGTGCAGTGGCCGGTAGGCTGATGGAAG
                STOP
TGGTGGACGAGTAC<u>TAG</u>GCTACCA (2338) TTCTGTCTTTGTTCACCGCAGATTCACAAGGGGTCTTCAGTGTTTGCGAGTGCAGTGGCCGGTAGGCTGATGGAAG
TGGTGGACGAGTAC<u>TAG</u>GCTACCA (2327) TTCTGTCTTTGTTCACCGCAGATTCACAAGGGGTCTTCAGTGTTTGCGAGTGCAGTGGCCGGTAGGCTGATGGAAG
TGGTGGACGAGTAC<u>TAG</u>GCTACCA (2388) TTCTGTCTTTGTTCACCGCAGATTCACAAGGGGTCTTCAGTGTTTGCGAGTGCAGTGGCCGGTAGGCTGATGGAAG
TGGTGGACGAGTAC<u>TAG</u>GCTACCA (2388) TTCTGTCTTTGTTCACCGCAGATTCACAAGGGGTCTTCAGTGTTTGCGAGTGCAGTGGCCGGTAGGCTGATGGAAG
TGGTGGACGAGTAC<u>TAG</u>GCTACCA (2388) TTCTGTCTTTGTTCACCGCAGATTCACAAGGGGTCTTCAGTGTTTGCGAGTGCAGTGGCCGGTAGGCTGATGGAAG
TGGTGGACGAGTAC<u>TAG</u>GCTACCA

```
                                                                      DAS-CMS31
```
(2438) TGCACTTGAATTTCTAGCTAGCTCTACGTACCGCGCTGCTATGAATCTAGCTATAGCGTTTCTTGGATGAAAGACT
AGTTAGTTGTTACCTTCTATCTTT (2438) TGCACTTGAATTTCTAGCTAGCTCTACGTACCGCGCTGCTATGAATCTAGCTATAGCGTTTCTTGGATGAAAGACT
AGTTAGTTGTTACCTTCTATCTTT (2427) TGCACTTGAATTTCTAGCTAGCTCTACGTACCGCGCTGCTATGAATCTAGCTATAGCGTTTCTTGGATGAAAGACT
AGTTAGTTGTTACCTTCTATCTTT (2488) TGCACTTGAATTTCTAGCTAGCTCTACGTACCGCGCTGCTATGAATCTAGCTATAGCGTTTCTTGGATGAAAGAAT
AGTTAGTTGTTACCTTCTATCTTT (2488) TGCACTTGAATTTCTAGCTAGCTCTACGTACCGCGCTGCTATGAATCTAGCTATAGCGTTTCTTGGATGAAAGAAT
AGTTAGTTGTTACCTTCTATCTTT

-continued (2488) TGCACTTGAATTTCTAGCTAGCTCTACGTACCGCGCTGCTATGAATCTAGCTATAGCGTTTCTTGGATGAAAGAAT
AGTTAGTTGTTACCTTCTATCTTT (2538) GCTTCAATTAAATCCGCTTGCTCGTTACAGACTGAGTTTGTTTCTAAATGTCAAGGTTGTTTTGGTCAAATTGAAT
AAATTGGCACACTGGCCTGTGAGG (2538) GCTTCAATTAAATCCGCTTGCTCGTTACAGACTGAGTTTGTTTCTAAATGTCAAGGTTGTTTTGGTCAAATTGAAT
AAATTGGCACACTGGCCTGTGAGG (2527) GCTTCAATTAAATCCGCTTGCTCGTTACAGACTGAGTTTGTTTCTAAATGTCAAGGTTGTTTTGGTCAAATTGAAT
AAATTGGCACACTGGCCTGTGAGG (2588) GCTTCAATTAAATCCGCTTGCTCGTTACAGACTGAGTTTGTTTCTAAATGTCAAGGTTGTTTTGGTCAAATTGAAT
AAATTGGCACACTGGCCTGTGAGG (2588) GCTTCAATTAAATCCGCTTGCTCGTTACAGACTGAGTTTGTTTCTAAATGTCAAGGTTGTTTTGGTCAAATTGAAT
AAATTGGCACACTGGCCTGTGAGG (2588) GCTTCAATTAAATCCGCTTGCTCGTTACAGACTGAGTTTGTTTCTAAATGTCAAGGTTGTTTTGGTCAAATTGAAT
AAATTGGCACACTGGCCTGTGAGG (2638) TTATTATATATATTTATGTGT-TTATTACTGGTCTATTAATTTGTCTTATTATTAATGTATTGCCTGTCAAGGAAT
DAS-CMS32
AAATGGTATGATGACCATATTTAT (2638) TTATTATATATATTTATGTGT-TTATTACTGGTCTATTAATTTGTCTTATTATTAATGTATTGCCTGTCAAGGAAT
AAATGGTATGATGACCATATTTAT (2627) TTATTATATATATTTATGTGT-TTATTACTGGTCTATTAATTTGTCCTATTATTAATGTATTGCCTGTCAAGGAAT
AAATGATATGATGACCATATTTAT (2688) TTATTATAT----TTATGTGTATTATTACTGGTCTATCAATTTGTCCTATTATT---GTATTGCCTGTCAAGGAAT
AAATTGTATGATGATCATATTTAT (2688) TTATTATAT----TTATGTGTATTATTACTGGTCTATCAATTTGTCCTATTATT---GTATTGCCTGTCAAGGAAT
AAATTGTATGATGATCATATTTAT (2688) TTATTATAT----TTATGTGTATTATTACTGGTCTATCAATTTGTCCTATTATT---GTATTGCCTGTCAAGGAAT
AAATTGTATGATGATCATATTTAT (2737) GCATAGATAGGATCGGATGAGTAGGTTCACTTGCTTGAGTTCACCGGTATAATTCCGG-------ATACATCTGGT
      DAS-CMS33
TAGGTCATCCTTTGGTCAGCTGCC (2737) GCATAGATAGGATCGGATGAGTAGGTTCACTTGCTTGAGTTCACCGGTATAATTCCGG-------ATACATCTGGT
TAGGTCATCCTTTGGTCAGCTGCC (2726) GCATAGATAGGA-----TGAGTAGGTTCACTTGCTTGAGTTCACCGGTATAATTCTGG-------ATACATCTGGT
TAGGTCATCCTTTGGTCAGCTGCC (2781) GCATAGATAGGA-----TGAGTAGGTTCACTTGCTTGAGTTCACCGGTATAATTCTGGTTTCTGGATACATCTGGT
TAGGTCAGCCTTTGGTCAGCTGCC (2781) GCATAGATAGGA-----TGAGTAGGTTCACTTGCTTGAGTTCACCGGTATAATTCTGGTTTCTGGATACATCTGGT
TAGGTCAGCCTTTGGTCAGCTGCC (2781) GCATAGATAGGA-----TGAGTAGGTTCACTTGCTTGAGTTCACCGGTATAATTCTGGTTTCTGGATACATCTGGT
TAGGTCAGCCTTTGGTCAGCTGCC (2830) CGCAAGCTTAACTCCGTGCGATATACAATATACAGATTTTATTATGGTTTTCCCCTGAACCTTCGTGACTAACTAT
GTTATCATTTTTATAGCTTTATAG (2830) CGCAAGCTTAACTCCGTGCGATATACAATATACAGATTTTATTATGGTTTTCCCCTGAACCTTCGTGACTAACTAT
GTTATCATTTTTATAGCTTTATAG (2814) CGCAA---------CGTGCGATATACAATATACATATTTTATTATGTTTTT----------TTCGTGACTAACTAT
GTTATCATTTTTATAGCTTTATAG (2876) CGCAAGCTTAACTCCGTGCGATATACACTATACAAATTTTATTATGTTTTT----------TTCGTGACTAACTAT
GTTATCATTTTTATAGCTTTATAG (2876) CGCAAGCTTAACTCCGTGCGATATACACTATACAAATTTTATTATGTTTTT----------TTCGTGACTAACTAT
GTTATCATTTTTATAGCTTTATAG (2876) CGCAAGCTTAACTCCGTGCGATATACACTATACAAATTTTATTATGTTTTT----------TTCGTGACTAACTAT
GTTATCATTTTTATAGCTTTATAG DAS-CMS34
(2930) TCTACAAACTGTTTTATACTCAGCTTGATAAGTACATTCTGGTTTGGACGATGG-TTTTTTTTTCTTGCAAAA-TG
AATTTGTCTTCAGCCTTTACGACT -continued

```
(2930) TCTACAAACTGTTTTATACTCAGCTTGATAAGTACATTCTGGTTTGGACGATGG-TTTTTTTTCTTGCAAAA-TG
       AATTTGTCTTCAGCCTTTACGACT (2895) TCTACAAACTGTTTTATACTCAGCTTGATAAGTACATTCTGGTTTGGACGAT----TTTTTTTCTTGCAAAAATG
       AATTTGTCTTCAGCCTTTACGACT (2966) TCTACAAACTGTTTTATACTCAGCTTGATAAGTACATTCTGGTTTGGACGATGGTTTTTTTTTCTTGCAAAAATG
       AATTTGTCTTCAGCCTTTACGACT (2966) TCTACAAACTGTTTTATACTCAGCTTGATAAGTACATTCTGGTTTGGACGATGGTTTTTTTTTCTTGCAAAAATG
       AATTTGTCTTCAGCCTTTACGACT (2966) TCTACAAACTGTTTTATACTCAGCTTGATAAGTACATTCTGGTTTGGACGATGGTTTTTTTTTCTTGCAAAAATG
       AATTTGTCTTCAGCCTTTACGACT (3028) ACATACAGTTTAGTT---------------TGTATTAATTGATACCGGAAGATCAGATTCGGACCACATATAAAC
       AAGGAATATATAGCACGTACTCGC (3028) ACATACAGTTTAGTT---------------TGTATTAATTGATACCGGAAGATCAGATTCGGACCACATATAAAC
       AAGGAATATATAGCACGTACTCGC (2991) ACATACAGTTTAGTTCTTAGAGTATCTCATCTGTATTAATTGATACCGGAAGA---GATTCGGGCCACATATAAAC
       AAGGAATATATAGCACGTACTCGC (3066) ACATACAGTTTAGTT---------------TGTATTAATTGATACCAGAAGATCAGATTCGGACCACATATAAAC
       AAGGAATATATAGCACGTACTCGC (3066) ACATACAGTTTAGTT---------------TGTATTAATTGATACCAGAAGATCAGATTCGGACCACATATAAAC
       AAGGAATATATAGCACGTACTCGC (3066) ACATACAGTTTAGTT---------------TGTATTAATTGATACCAGAAGATCAGATTCGGACCACATATAAAC
       AAGGAATATATAGCACGTACTCGC (SEQ ID NO: 5)
(3112) TGAACCTTAAATATAGTCAGGAAAATAGAGGGTTAACTAAACCGATCCAGAAACCAATTACATTGATATTGACTCT
       ATTCTTCGTT (SEQ ID NO: 6)
(3112) TGAACCTTAAATATAGTCAGGAAAATAGAGGGTTAACTAAACCGATCCAGAAACCAATTACATTGATATTGACTCT
       ATTCTTCGTT (SEQ ID NO: 7)
(3088) TGAACCTTAAATATAGTCAGGAACATAGAGGGTTAACTAAACCGATCCAGAAACCAATTACATTGATATTGACTCT
       ATTCTTCGTT (SEQ ID NO: 8)
(3150) TGAACCTTAAATATAGTCAGGAACATAGAGGGTTAACTAAACCGATCCAGAAACCAATTACATTGATATTGACTCT
       ATTCTTCGTT (SEQ ID NO: 9)
(3150) TGAACCTTAAATATAGTCAGGAACATAGAGGGTTAACTAAACCGATCCAGAAACCAATTACATTGATATTGACTCT
       ATTCTTCGTT (SEQ ID NO: 10)
(3150) TGAACCTTAAATATAGTCAGGAACATAGAGGGTTAACTAAACCGATCCAGAAACCAATTACATTGATATTGACTCT
       ATTCTTCGTT
```

The translation start and stop codons and positions for markers DAS-CMS21 through DAS-CMS35 within the gene are underlined and/or labeled.

Gene specific assay design and validation. Alignments of predicted Rf4-bHLH protein sequences indicated that all three restorer lines had identical protein sequences and non-restorer lines were identical (data not shown). There were four amino-acid changes between restorer lines and non-restorer lines: His ($H_{103}$) to Asn ($N_{103}$), Ala ($A_{130}$) insertion, Pro ($P_{266}$) to Leu ($L_{267}$) and Tyr ($Y_{186}$) to Phe ($F_{187}$) substitution in the restorer lines. In comparison with other monocot orthologs, the Phe ($F_{187}$) substitution in the maize restorer allele was conserved, and the other three amino acid changes were less conserved and were located in variable sites (data not shown). This conserved substitution was used for gene specific TaqMan® assay design.

```
SEQ ID NO: 6 primer sequences for an CMS-C line
Forward primer            5'-CAACGGCGTCGAGAAGAAG-3'       (SEQ ID NO: 11)

VIC Reporter              5'-CTCGGCGTCGGCCGCGACGAAGAG-3'  (SEQ ID NO: 12)

rf4(non-restorer)probe-MGB 5'-ACCGAGAAGTACACCGC-3'        (SEQ ID NO: 13)

Reverse primer            5'-ATTGCAACCCATACTCCACGTA-3'    (SEQ ID NO: 14)

SEQ ID NO: 8 primer sequences for an Rf4 line
Forward primer            5'-CAACGGCGTCGAGAAGAAG-3'       (SEQ ID NO: 15)
```

```
FAM Reporter              5'-TCGGCGTCGGCCGCGACGAAGAG-3'  (SEQ ID NO: 16)

Rf4 (restorer) specific   5'-CACCGAGAAGTTTACGGC-3'       (SEQ ID NO: 17)
probe-MGB Reverse primer            5'-ATTGCAACCCATACTCCACGTA-3'   (SEQ ID NO: 18)
```

Figure 1B:
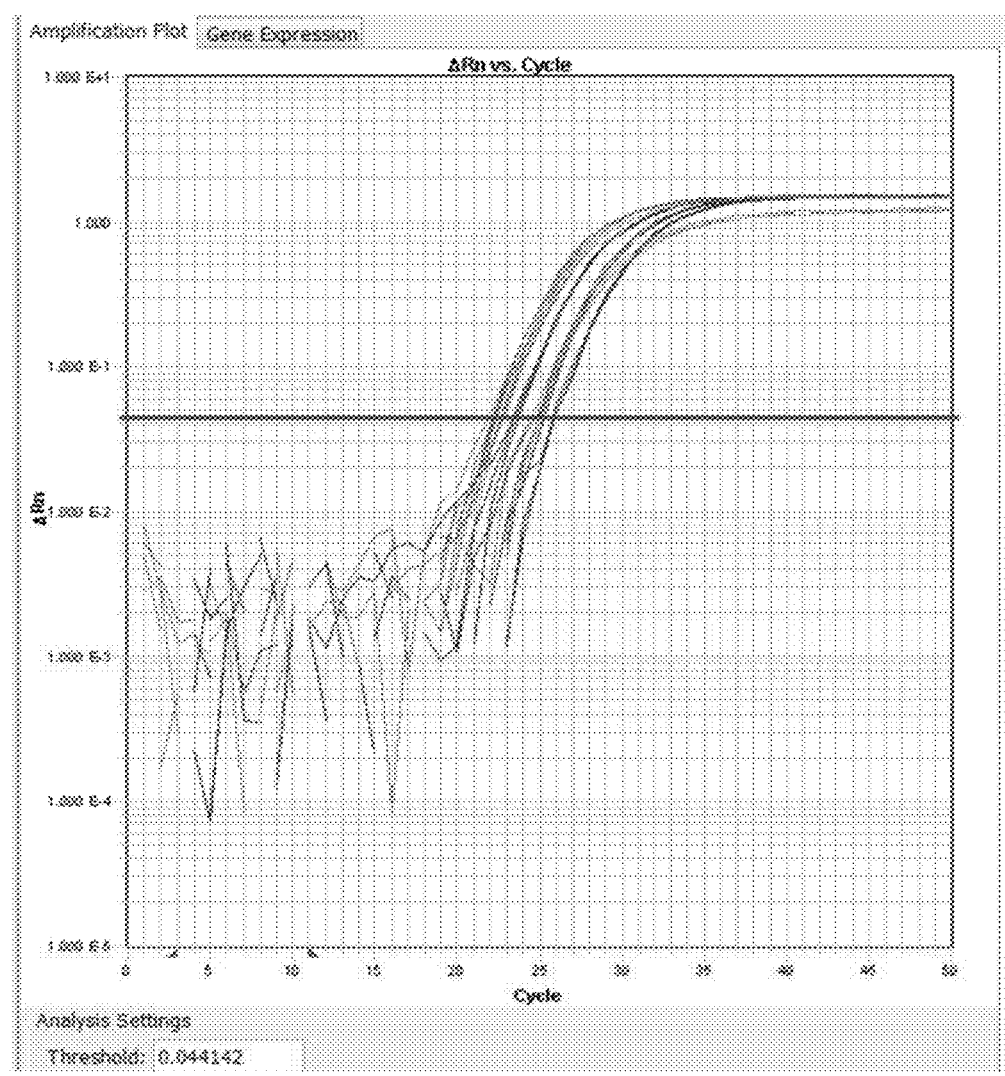
FIG. 1B. Real-time PCR amplification plots with relative fluorescence unit (RFU) are shown for Rf4 with CMS-C and non-restorer with VIC. Exponential amplification phase was observed from cycles 23 to 35 for both Rf4 and CMS-C or non-restorer genes.

Three known Rf4 restoration lines and six non-restoration lines were used for assay testing. One hemizygous sample was made by combining equal amount of DNA from Rf4 line with a CMS-C line. Real-time PCR was used to test the efficiency of the assay. Oligonucleotides specific to the Rf4 gene and to the corresponding CMS-C line or non-restorer were combined in the same assay. FAM was used to monitor the Rf4 amplicon from the restorer lines and VIC from non-restorer CMS-C or non-restorer lines. Exponential amplification phase was observed from cycles 23 to 35 for both Rf4 restorer lines and non-restorer CMS-C or non-restorer lines (FIGS. 1A and 1B).

Validation of end-point TaqMan® zygosity analysis. An F2 CMS-C/restoration mapping population with 500 individuals was used to validate the assay using end-point TaqMan® PCR instead of using real-time TaqMan® PCR. The advantages of end-point TaqMan® over real-time TaqMan® include its ease to use and high throughput. For end-point TaqMan® PCR, any regular PCR machine that can fit 96- or 384-well plates plus a plate reader that can read FAM and VIC are sufficient to perform the assay.

Figure 2:
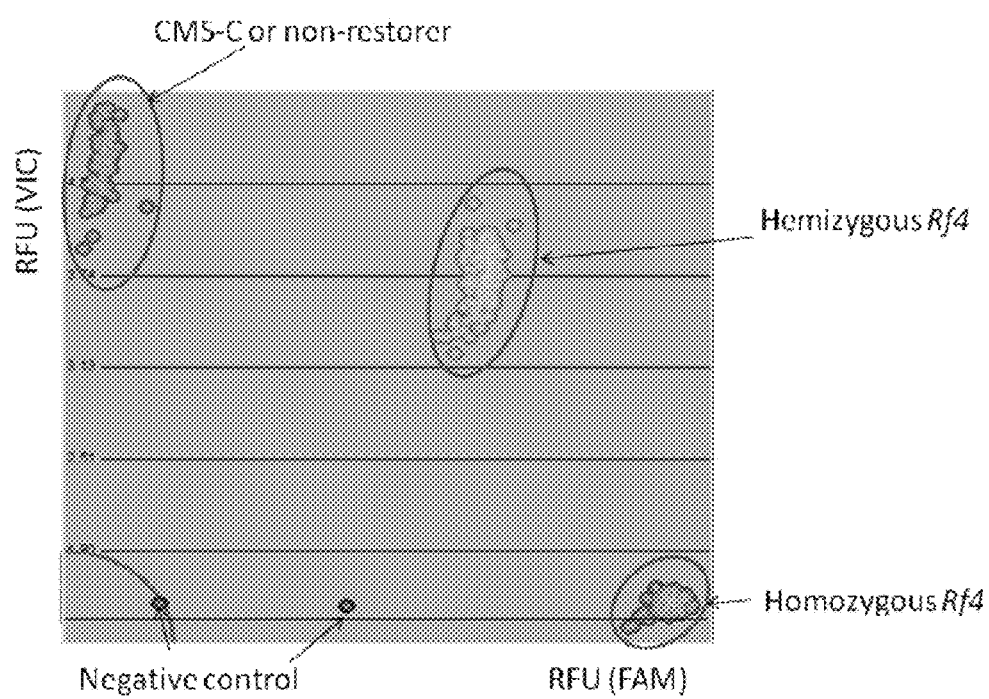
FIG. 2. Rf4 zygosity test with end-point TaqMan assay using KLIMS. The raw fluorescence intensity data directly from the plate reader was analyzed in KLIMS. A graph with RFU of FAM as x-axis and VIC as y-axis was generated. Zygosity calls were made based on the cluster separation in a cluster view.

Following completion of the TaqMan® PCR and fluorescence reading, the raw fluorescence intensity data directly from the plate reader were analyzed in the KLIMS system. A graph with RFU (relative fluorescence unit) of FAM as x-axis and VIC as y-axis was generated. Zygosity calls were made based on the cluster separation in a cluster view (FIG. 2). Since FAM was used to monitor the amplification of Rf4 from restorer lines and VIC for non-restorer/CMS-C lines, samples with strong signals of FAM and little or no VIC are homozygous for Rf4 allele; samples with strong signals of VIC and little or no FAM are non-restorer/CMS-C lines (nulls); and samples with strong signals of both FAM and VIC are hemizygous for Rf4 allele.

F2 genotypic data based on the Rf4 gene specific end-point TaqMan® PCR assay matched completely with field phenotypic data, which demonstrated the effectiveness and accuracy of the end-point TaqMan® PCR assay for testing Rf4 zygosity in a high throughput way. This assay enables large scale and high throughput screening of maize germplasms with the Rf4 restoration gene. This assay will also increase the scale of using a CMS-C/Rf4 system for hybrid corn seed production.

The invention claimed is:

1. A PCR assay method for determining zygosity of an Rf4 gene in a corn plant, the method comprising:
   (a) performing a first PCR assay using a first probe, a first forward primer, and a first reverse primer on a polynucleotide from a corn plant sample, wherein the first probe is SEQ ID NO:3;
   (b) performing a second PCR assay using a second probe, a second forward primer, and a second reverse primer on the polynucleotide sample, wherein the second probe is SEQ ID NO:4;
   (c) quantifying the first probe and the second probe; and,
   (d) comparing the quantified first probe and the quantified second probe of the first PCR assay and the second PCR assay to determine the zygosity,
   wherein the zygosity of the Rf4 gene in the corn plant is selected from the group consisting of homozygous, heterozygous, hemizygous, and nullizygous.

2. The PCR assay method of claim 1, wherein the first and the second PCR assays are a multiplex PCR-format.

3. The PCR assay method of claim 2, wherein the first and second PCR assays are performed in a single PCR assay tube.

4. The PCR assay method of claim 1, wherein the first and the second PCR assays are a real-time PCR.

5. The PCR assay method of claim 1, the method further comprising:
   loading a PCR reaction mixture in a PCR assay tube;
   wherein the PCR reaction mixture comprises a polymerase with 5' to 3' nuclease activity, deoxynucleotides, a buffer, the first forward primer and the second forward primer, the first reverse primer and the second reverse primer, the first probe and the second probe, and the polynucleotide sample,
   wherein the first probe and the second probe comprising fluorescent dyes with distinguishable excitation/emission spectra; and
   wherein the first PCR assay and the second PCR assay include an amplification step under amplification conditions such that the 5' to 3' nuclease activity of the polymerase cleaves the first probe and the second probe of claim 1, thereby releasing the fluorescent dyes comprising distinguishable excitation/emission spectra.

6. The PCR assay method of claim 1, further comprising:
   loading a PCR reaction mixture in a PCR assay tube,
   wherein the PCR reaction mixture comprises a polymerase with 5' to 3' nuclease activity, deoxynucleotides, a buffer, the first forward primer or the second forward primer, the first reverse primer or the second reverse primer, the first probe or the second probe, and the polynucleotide sample; and
   wherein the first PCR assay and the second PCR assay include an amplification step under conditions such that the 5' to 3' nuclease activity of the polymerase cleaves the first probe or the second probe, thereby releasing fluorescent dyes comprising distinguishable excitation/emission spectra.

7. The PCR assay method of claim 1, wherein the first probe and the second probe are quantified by measuring excitation/emission spectra emitted from the fluorescent dyes, during the amplification.

8. The PCR assay method of claim 1, wherein zygosity is determined by comparing the quantified first probe and the second probe using a $\Delta\Delta Ct$ formula.

9. The PCR assay method of claim 1, wherein the first forward primer comprises SEQ ID NO:1.

10. The PCR assay method of claim 1, wherein the first reverse primer comprises SEQ ID NO:2.

11. The PCR assay method of claim 1, wherein the first probe comprises a first fluorescent dye and a first quencher.

12. The PCR assay method of claim 11, wherein the first fluorescent dye comprises a hexachloro-fluorescein fluorescent dye, a fluorescent dye with an absorbance maximum of 538 nm and an emission maximum of 554 nm, a fluorescein fluorescent dye, a 4',5'-dichloro-2',7'-dimethoxyfluorescein fluorescent dye, a tetrachloro-fluorescein fluorescent dye, a cyanine3 fluorescent dye, a cyanine3.5 fluorescent dye, a cyanine5 fluorescent dye, a cyanine5.5 fluorescent dye, a cyanine7 fluorescent dye, or a carboxy-X-rhodamine fluorescent dye.

13. The PCR assay method of claim 11, wherein the first quencher comprises a 4-((4-(dimethylamino)phenyl)azo) benzoic acid quencher, a 5-Carboxytetramethylrhodamine quencher, a Maleimide (2,5-Pyrroledione) quencher, an azo bond and 1,3,3-trimethyl-2-methyleneindoline ring system quencher, an azo bond and 1,3,3-trimethyl-2-methyleneindoline ring system quencher, a 3,3'-((2-((E)-2-(5-((E)-2-(3-(5-carboxypentyl)-1,1-dimethyl-7-sulfonato-1H-benzo[e]

indol-3-ium-2-yl)vinyl)-3-chlorocyclohex-3-en-1-yl)vinyl)-3,3-dimethyl-1-(3-sulfonatopropyl)-3H-indol-1-ium-5-yl)azanediyl)bis(propane-1-sulfonate)quencher, a dihydrocyclopyrroloindole tripeptide Minor Groove Binding quencher, or a 4'-(2-Nitro-4-toluyldiazo)-2'-methoxy-5'-methyl-azobenzene-4"-(N-ethyl)-N-ethyl-2-cyanoethyl-(N,N-diisopropyl)-phosphoramidit quencher.

14. The PCR assay method of claim 11, wherein the first probe comprises fluorescein as the first fluorescent dye at the 5' end of the first probe and dihydrocyclopyrroloindole tripeptide Minor Groove Binding quencher as the first quencher on the 3' end of the first probe.

15. The PCR assay method of claim 1, wherein the second forward primer comprises SEQ ID NO:1.

16. The PCR assay method of claim 1, wherein the second reverse primer comprises SEQ ID NO:2.

17. The PCR assay method of claim 1, wherein the second probe comprises a second fluorescent dye and a second quencher.

18. The PCR assay method of claim 17, wherein the second fluorescent dye is selected from the group consisting of a hexachloro-fluorescein fluorescent dye, a fluorescein fluorescent dye, a fluorescent dye with an absorbance maximum of 538 nm and an emission maximum of 554 nm, a 4',5'-dichloro-2',7'- dimethoxyfluorescein fluorescent dye, a tetrachloro-fluorescein fluorescent dye, a cyanine 3 fluorescent dye, a cyanine 3.5 fluorescent dye, a cyanine 5 fluorescent dye, a cyanine 5.5 fluorescent dye, a cyanine 7 fluorescent dye, or a carboxy-X-rhodamine fluorescent dye.

19. The PCR assay method of claim 17, wherein the second quencher is selected from the group consisting of a 4-((4-(dimethylamino)phenyl)azo)benzoic acid quencher, a 5-Carboxytetramethylrhodamine quencher, a Maleimide (2,5-Pyrroledione) quencher, an azo bond and 1,3,3-trimethyl-2-methyleneindoline ring system quencher, an azo bond and 1,3,3-trimethyl-2-methyleneindoline ring system quencher, a 3,3'-((2-(((E)-2-(5((E)-2-(3-(5-carboxypentyl)-1,1-dimethyl-7-sulfonato-1H-benzo[e]indol-3-ium-2-yl)vinyl)-3-chlorocyclohex-3-en-1-yl)vinyl)-3,3-dimethyl-1-(3-sulfonatopropyl)-3H-indol-1-ium-5-yl)azanediyl)bis(propane-1-sulfonate)quencher, a dihydrocyclopyrroloindole tripeptide Minor Groove Binding quencher, and a 4'-(2-Nitro-4-toluyldiazo)-2'-methoxy-5'-methyl-azobenzene-4"-(N-ethyl)-N-ethyl-2-cyanoethyl-(N,N-diisopropyl)-phosphoramidit quencher.

20. The PCR assay method of claim 17, wherein the second probe comprises a fluorescent dye with an absorbance maximum of 538 nm and an emission maximum of 554 nm as the second fluorescent dye at the 5' end of the second probe, and dihydrocyclopyrroloindole tripeptide Minor Groove Binding quencher as the second quencher on the 3' end of the second probe.

21. The PCR assay method of claim 1, wherein the Rf4 gene comprises a dinucleotide substitution at nucleotide positions 1664-1665 at any one of Rf4-bHLH genomic sequences SEQ ID NOS. 5-10 (at amino acid positions 186-187).

22. The PCR assay method of claim 1, wherein the corn plant comprises an Rf4 dinucleotide substitution at nucleotide positions 1664-1665 at any one of Rf4-bHLH genomic sequences SEQ ID NOS. 5-10 (at amino acid positions 186-187).

23. The PCR assay method of claim 1, wherein the corn plant is a maize germplasm.

24. The PCR assay method of claim 1, wherein the corn plant sample is selected from the group consisting of a plant part, a plant organ, a plant seed, and a plant cell.

25. The PCR assay method of claim 24, wherein the plant part is selected from the group consisting of leaves, pollen, embryos, cotyledons, hypocotyls, meristematic cells, roots, root tips, anthers, flowers, stems, and pods.

26. The PCR assay method of claim 1, further comprising the step of breeding introgression of the line of the corn plant into a second line of *Zea mays*.

27. The PCR assay method of claim 26, wherein the second line of *Zea mays* does not contain the Rf4 allele.

28. The PCR assay method of claim 26, wherein the method detects the presence or absence of the Rf4 allele within a progeny plant of the breeding introgression.

29. The PCR assay method of claim 1, wherein the method is used to identify lines of *Zea mays* that possess restored male fertility.

30. The PCR assay method of claim 1, wherein the first forward primer comprises SEQ ID NO:11.

31. The PCR assay method of claim 1, wherein the first reverse primer comprises SEQ ID NO:14.

32. The PCR assay method of claim 1, wherein the second forward primer comprises SEQ ID NO:11.

33. The PCR assay method of claim 1, wherein the second reverse primer comprises SEQ ID NO:14.

34. The PCR assay method of claim 1, wherein the first forward primer comprises SEQ ID NO:15.

35. The PCR assay method of claim 1, wherein the first reverse primer comprises SEQ ID NO:18.

36. The PCR assay method of claim 1, wherein the second forward primer comprises SEQ ID NO:15.

37. The PCR assay method of claim 1, wherein the second reverse primer comprises SEQ ID NO:18.

* * * * *

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caacggcgtc gagaagaag                                                    19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taacgttggg tatgaggtgc at                                                22

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
accgagaagt acaccgc                                                      17
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 4
caccgagaag tttacggc                                                    18

<210> SEQ ID NO 5
<211> LENGTH: 3197
<212> TYPE: DNA
<213> ORGANISM: Zea mays

<400> SEQUENCE: 5

| | | | | | | |
|---|---|---|---|---|---|---|
| ggcaagctaa | tgggtacat | atggaaggag | gaaaccaagt | cgatcgtcgt | cgtagcatgt | 60 |
| cggtgtgggt | actacactac | acacacatat | acatgggcaa | cgcaaggcca | cctttctgaa | 120 |
| tcctgcatga | gcgtgtacca | ctagaattgt | cagtgtgtgc | ggtgtatggc | aggtttttgg | 180 |
| ttcggcaagt | ggggccctcc | ggggaggaat | ctcagtaaca | aaccgctctt | ctgaaaaggt | 240 |
| cagccatccc | cggtccggtc | cggtgatgtc | gtcgctgtcg | ctctgctagc | ttgctgccga | 300 |
| tccccccccc | ccccccccc | cttcttctct | ctacccctcc | ctccacctca | taaatactta | 360 |
| gtttaataac | cttgcactgc | cgcagtagcc | cttaactgct | gctatctatc | tcttttctga | 420 |
| aggaaaaaaa | aggtttgata | ctcctctacc | tagctagtcc | tgcatgccgc | taatgtgcgt | 480 |
| cttgcctgtt | tatttgttct | taataagggc | tgcctatcta | ttatattttg | cacctgtttt | 540 |
| gctgtgttct | tggtaactag | cttaattcct | tcgcctacaa | tcgtcaaatc | cccccccatca | 600 |
| tcagtcagat | gaacttttga | tcgaattgaa | gttgttcttc | taattcggcc | ccagcagcgc | 660 |
| ccatgcatct | ggttttattt | gctttctgtt | gggtataata | tgcaagacct | tttgttgcta | 720 |
| gggcaaggct | gcaaccacat | gcgtgtactg | aactcatgat | gtaactcatc | cttttgttt | 780 |
| gctcacagaa | tcactactct | actgcacttc | cttttcatcc | gatccgcaat | cttttttttc | 840 |
| ttttacatgc | tttagttttc | tctctttctt | gattacaaac | atgattactg | gaactttctt | 900 |
| aggctgcctt | ccccttcctt | ggatctgctt | tagttttctt | ttttgggcta | ccgcgcgcgg | 960 |
| cttatttgag | tttatcactt | gctgcatata | cataatatat | atatacatgc | atgcgatggc | 1020 |
| gttcatgtta | ctcaactaca | gatctgtttc | tgttcgtgtg | tttcagttca | gcgcgcagtt | 1080 |
| aagcatagca | ggacgaccac | gacgatgtat | cacccgcagt | gcgagctcct | gacgatggcg | 1140 |
| cacgaaacgc | cggacctgga | cgccggccag | ccgcacctaa | ccgtctccgg | cgtcgccagc | 1200 |
| atcccggcag | agctgagctt | ccacctgctg | cactcgctcg | acgccgcggc | ggcggtcaat | 1260 |
| cccgtcacgg | cgccgccgca | gtccaccatc | gactacttcc | tcggcggcgc | cgatccccac | 1320 |
| cagcaggcca | tgcagtacga | gccgctgccg | ccgccgcgg | gcggccacca | ccagtacacc | 1380 |
| atggacatgt | tccgcgacta | ctgcgacggc | cactacccca | ccgccgagcc | gtacatccgc | 1440 |
| gggacaatga | ctggagccct | cgtgttcggg | gccaccgacg | acgacgactc | ggccgctgcc | 1500 |
| tacatgcccg | gggggcactt | tgagacctcc | ccgccgccgc | cacgcgccac | cggccgcggc | 1560 |
| aggaagcggg | gcagggcgct | gggcggcggc | ttccatgctg | tgctggccaa | cggcgtcgag | 1620 |
| aagaaggaga | agcagcgccg | gctgcggctc | accgagaagt | acaccgccct | catgcacctc | 1680 |
| atacccaacg | ttacaaaggt | cgtaccaaat | cctcctctta | tgttcgtcca | tcgtttcaaa | 1740 |

```
ttaagttaaa aaattaattc acggttcttg ttgtttattt tttgcgcact gcagactgat    1800
agggcgacgg tgatctcgga cgcgatcgag tacatccagg agctggggag gacggtggag    1860
gagctgacgc tgctggtgga aagaagcgg cgccggaggg agctgcaggg ggacgtcgtg    1920
gacgcggcgc cggctgcggt ggttgctgcc gccggtgagg cggagagctc ggagggcgag    1980
gtggctcctc cgccgccggc cgtgccgcgg cagccgatcc ggagcacgta catccagcgg    2040
cggagcaagg acacgtccgt ggacgtgcgg atcgtggagg aggacgtgaa catcaagctc    2100
accaagcgcc ggcgcgacgg gtgcctcgca gccgcgtcgc gcgcgctgga tgacctccgc    2160
cttgacctcg tccacctctc cggcggcaag atcggtgact gtcaaatcta catgttcaac    2220
accaaggtac atacgaatac gatacgtagc cattgatcga tctgtaattc tgtagcctga    2280
cgattccgag gtttctggtg ctaaaaaatg catcttttt tctcagatga caatgctttc    2340
tgtctttgtt caccgcagat tcacaagggg tcttcagtgt ttgcgagtgc agtggccggt    2400
aggctgatgg aagtggtgga cgagtactag gctaccatgc acttgaattt ctagctagct    2460
ctacgtaccg cgctgctatg aatctagcta tagcgtttct tggatgaaag actagttagt    2520
tgttaccttc tatctttgct tcaattaaat ccgcttgctc gttacagact gagtttgttt    2580
ctaaatgtca aggttgtttt ggtcaaattg aataaattgg cacactggcc tgtgaggtta    2640
ttatatatat ttatgtgttt attactggtc tattaatttg tcttattatt aatgtattgc    2700
ctgtcaagga ataaatggta tgatgaccat atttatgcat agataggatc ggatgagtag    2760
gttcacttgc ttgagttcac cggtataatt ccggatacat ctggttaggt catcctttgg    2820
tcagctgccc gcaagcttaa ctccgtgcga tatacaatat acagatttta ttatggtttt    2880
ccctgaacc ttcgtgacta actatgttat catttttata gctttatagt ctacaaactg    2940
ttttatactc agcttgataa gtacattctg gtttggacga tggtttttt ttcttgcaaa    3000
atgaatttgt cttcagcctt tacgactaca tacagtttag tttgtattaa ttgataccgg    3060
aagatcagat tcggaccaca tataaacaag gaatatatag cacgtactcg ctgaacctta    3120
aatatagtca ggaaaatag gggttaacta aaccgatcca gaaaccaatt acattgatat    3180
tgactctatt cttcgtt                                                   3197
```

<210> SEQ ID NO 6
<211> LENGTH: 3197
<212> TYPE: DNA
<213> ORGANISM: Zea mays

<400> SEQUENCE: 6

```
ggcaagctaa tggggtacat atggaaggag gaaaccaagt cgatcgtcgt cgtagcatgt      60
cggtgtgggt actacactac acacacatat acatgggcaa cgcaaggcca cctttctgaa     120
tcctgcatga gcgtgtacca ctagaattgt cagtgtgtgc ggtgtatggc aggttttggg    180
ttcggcaagt ggggccctcc ggggaggaat ctcagtaaca aaccgctctt ctgaaaaggt    240
cagccatccc cggtccggtc cggtgatgtc gtcgctgtcg ctctgctagc ttgctgccga    300
tccccccccc cccccccccc cttcttctct ctaccctcc ctccacctca taaatactta     360
gtttaataac cttgcactgc cgcagtagcc ttaactgct gctatctatc tcttttctga     420
aggaaaaaaa aggtttgata tcctctacc tagctagtcc tgcatgccgc taatgtgcgt    480
cttgcctgtt tatttgttct taataagggc tgcctatcta ttatattttg cacctgtttt    540
gctgtgttct tggtaactag cttaattcct tcgcctacaa tcgtcaaatc ccccccatca    600
tcagtcagat gaacttttga tcgaattgaa gttgttcttc taattcggcc ccagcagcgc    660
```

```
ccatgcatct ggttttattt gctttctgtt gggtataata tgcaagacct tttgttgcta      720
gggcaaggct gcaaccacat gcgtgtactg aactcatgat gtaactcatc cttttttgttt     780 gctcacagaa tcactactct actgcacttc cttttcatcc gatccgcaat ctttttttttc     840 ttttacatgc tttagttttc tctcttctt gattacaaac atgattactg aactttctt       900 aggctgcctt cccttcctt ggatctgctt tagttttctt ttttgggcta ccgcgcgcgg       960
cttatttgag tttatcactt gctgcatata cataatatat atatacatgc atgcgatggc     1020
gttcatgtta ctcaactaca gatctgtttc tgttcgtgtg tttcagttca gcgcgcagtt    1080
aagcatagca ggacgaccac gacgatgtat cacccgcagt gcgagctcct gacgatggcg    1140
cacgaaacgc cggacctgga cgccggccag ccgcacctaa ccgtctccgg cgtcgccagc    1200
atcccggcag agctgagctt ccacctgctg cactcgctcg acgccgcggc ggcggtcaat    1260
cccgtcacgg cgccgccgca gtccaccatc gactacttcc tcggcggcgc cgatccccac    1320
cagcaggcca tgcagtacga gccgctgccg ccgccgcgg gcggccacca ccagtacacc    1380
atggacatgt tccgcgacta ctgcgacggc cactacccca ccgccgagcc gtacatccgc    1440
gggacaatga ctggagccct cgtgttcggg gccaccgacg acgacgactc ggccgctgcc    1500
tacatgcccg gggggcactt tgagacctcc ccgccgccgc cacgcgccac cggccgcggc    1560
aggaagcggg gcagggcgct gggcggcggc ttccatgctg tgctggccaa cggcgtcgag    1620
aagaaggaga agcagcgccg gctgcggctc accgagaagt acaccgccct catgcacctc    1680 atcccaacg ttacaaaggt cgtaccaaat cctcctctta tgttcgtcca tcgtttcaaa     1740
ttaagttaaa aaattaattc acggttcttg ttgtttattt tttgcgcact gcagactgat    1800
agggcgacgg tgatctcgga cgcgatcgag tacatccagg agctggggag gacggtggag    1860
gagctgacgc tgctggtgga gaagaagcgg cgccggaggg agctgcaggg ggacgtcgtg    1920
gacgcggcgc cggctgcggt ggttgctgcc gccggtgagg cggagagctc ggagggcgag    1980
gtggctcctc cgccgccggc cgtgccgcgg cagccgatcc ggagcacgta catccagcgg    2040
cggagcaagg acacgtccgt ggacgtgcgg atcgtggagg aggacgtgaa catcaagctc    2100
accaagcgcc ggcgcgacgg gtgcctcgca gccgcgtcgc gcgcgctgga tgacctccgc    2160
cttgacctcg tccacctctc cggcggcaag atcggtgact gtcaaatcta catgttcaac    2220
accaaggtac atacgaatac gatacgtagc cattgatcga tctgtaattc tgtagcctga    2280
cgattccgag gtttctggtg ctaaaaatg catctttttt tctcagatga caatgctttc    2340
tgtctttgtt caccgcagat tcacaagggg tcttcagtgt ttgcgagtgc agtggccggt    2400
aggctgatgg aagtggtgga cgagtactag gctaccatgc acttgaattt ctagctagct    2460
ctacgtaccg cgctgctatg aatctagcta tagcgtttct tggatgaaag actagttagt    2520
tgttaccttc tatctttgct tcaattaaat ccgcttgctc gttacagact gagtttgttt    2580
ctaaatgtca aggttgtttt ggtcaaattg aataaattgg cacactggcc tgtgaggtta    2640
ttatatatat ttatgtgttt attactggtc tattaatttg tcttattatt aatgtattgc    2700
ctgtcaagga ataaatggta tgatgaccat atttatgcat agataggatc ggatgagtag    2760
gttcacttgc ttgagttcac cggtataatt ccggatacat ctggttaggt catcctttgg    2820
tcagctgccc gcaagcttaa ctccgtgcga tatacaatat acagatttta ttatggtttt    2880
cccctgaacc ttcgtgacta actatgttat catttttata gctttatagt ctacaaactg    2940
ttttatactc agcttgataa gtacattctg gtttggacga tggttttttt ttcttgcaaa    3000
```

| | |
|---|---|
| atgaatttgt cttcagcctt tacgactaca tacagtttag tttgtattaa ttgataccgg | 3060 |
| aagatcagat tcggaccaca tataaacaag gaatatatag cacgtactcg ctgaaccttta | 3120 |
| aatatagtca ggaaaataga gggttaacta aaccgatcca gaaaccaatt acattgatat | 3180 |
| tgactctatt cttcgtt | 3197 |

<210> SEQ ID NO 7
<211> LENGTH: 3173
<212> TYPE: DNA
<213> ORGANISM: Zea mays

<400> SEQUENCE: 7

| | |
|---|---|
| ggcaagctaa tggggtacat atggaaggag gaaaccaagt cgatcgtcgt cgtagcatgt | 60 |
| cggtgtgggt actacactac acacacatat acatgggcaa cgcaaggcca cctttctgaa | 120 |
| tcctgcatga gcgtgtacca ctagaattgt cagtgtgtgc ggtgtatggc aggttttttgg | 180 |
| ttcggcaagt ggggccctcc ggggaggaat ctcagtaaca aaccgctctt ctgaaaaggt | 240 |
| cagccatccc cggtccggtc cggtgatgtc gtcgctgtcg ctctgctagc ttgctgccga | 300 |
| tcccccccc ttcttctctc tacccctccc tccacctcat aaatacttag tttaataacc | 360 |
| ttgcactgcc gcagtagccc ttaactgctg ctatctatct cttttctgaa ggaaaaaaaa | 420 |
| ggtttgatac tcctctacct agctagtcct gcatgccgct aatgtgcgtc ttgcctgttt | 480 |
| atttgttctt aataagggct gcctatctat tatattttgc acctgttttg ctgtgttctt | 540 |
| ggtaactagc ttaattcctt tgcctacaat cgtcaaatcc cccccatcat cagtcagatg | 600 |
| aacttttgat cgaattgaag ttgttcttct aattcggccc cagcagcgcc catgcatctg | 660 |
| gttttatttg ctttctgttg ggtataatat gcaagacctt tgttgctag ggcaaggctg | 720 |
| caaccacatg cgtgtactga actcatgatg taactcatcc ttttttgtttg ctcacagaat | 780 |
| cactactcta ctgcacttcc ttttcatccg atccgcaatc tttttttttct tttacatgct | 840 |
| ttagttttct ctctttcttg attacaaaca tgattactgg aactttctta ggctgccttc | 900 |
| cccttccttg gatctgcttt agttttcttt tttgggctac cgcgcgcggc ttatttgagt | 960 |
| ttatcacttg ctgcatatac ataatatata tatacatgca tgcgatggcg ttcatgttac | 1020 |
| tcaactacag atctgtttct gttcgtgtgt ttcagttcag cgcgcagtta agcatagcag | 1080 |
| gacgaccacg acgatgtatc acccgcagtg cgagctcctg acgatggcgc acgaaacgcc | 1140 |
| ggacctggac gccggccagc cgcacctaac cgtctccggc gtcgccagca tcccggcaga | 1200 |
| gctgagcttc cacctgctgc actcgctcga cgccgcggcg gcggtcaatc ccgtcacggc | 1260 |
| gccgccgcag tccaccatcg actacttcct cggcggcgcc gatccccacc agcaggccat | 1320 |
| gcagtacgag ccgctgccgc cgccgcgggg cggccaccac cagtacacca tggacatgtt | 1380 |
| ccgcgactac tgcgacggcc actaccccac cgccgagccg tacatccgcg ggacaatgac | 1440 |
| tggagccctc gtgttcgggg ccaccgacga cgacgactcg gccgctgcct acatgcccgg | 1500 |
| ggggcacttt gagacctccc cgccgccgcc acgcgccacc ggccgcggca ggaagcgggg | 1560 |
| cagggcgctg ggcggcggct tccatgctgt gctggccaac ggcgtcgaga agaaggagaa | 1620 |
| gcagcgccgg ctgcggctca ccgagaagta caccgccctc atgcacctca tcccaacgt | 1680 |
| tacaaaggtc gtaccaaatc ctcctcttat gttcgtccat cgtttgaaat taagttaaaa | 1740 |
| aattaattca cggttcttgt tgtttatttt ttgcgcactg cagactgata gggcgacggt | 1800 |
| gatctcggac gcgatcgagt acatccagga gctggggagg acggtggagg agctgacgct | 1860 |
| gctggtggag aagaagcggc gccggaggga gctgcagggg gacgtcgtgg acgcggcgcc | 1920 |

```
ggctgcggtg gttgctgccg ccggtgaggc ggagagctcg gagggcgagg tggctcctcc      1980
gccgccggcc gtgccgcggc agccgatccg gagcacgtac atccagcggc ggagcaagga      2040
cacgtccgtg gacgtgcgga tcgtggagga ggacgtgaac atcaagctca ccaagcgccg      2100
gcgcgacggg tgcctcgcag ccgcgtcgcg cgcgctggat gacctccgcc ttgacctcgt      2160
ccacctctcc ggcggcaaga tcggtgactg tcaaatctac atgttcaaca ccaaggtaca      2220
tacgaatacg atacgtagcc attgatcgat ctgtaattct gtagcctgac gattccgagg      2280
tttctggtgc taaaaaatgc atctttttt ctcagatgac aatgctttct gtctttgttc       2340
accgcagatt cacaaggggt cttcagtgtt tgcgagtgca gtggccggta ggctgatgga      2400
agtggtggac gagtactagg ctaccatgca cttgaatttc tagctagctc tacgtaccgc      2460
gctgctatga atctagctat agcgtttctt ggatgaaaga ctagttagtt gttaccttct      2520
atctttgctt caattaaatc cgcttgctcg ttacagactg agtttgtttc taaatgtcaa      2580
ggttgttttg gtcaaattga ataaattggc acactggcct gtgaggttat tatatatatt      2640
tatgtgttta ttactggtct attaatttgt cctattatta atgtattgcc tgtcaaggaa      2700
taaatgatat gatgaccata tttatgcata gataggatga gtaggttcac ttgcttgagt      2760
tcaccggtat aattctggat acatctggtt aggtcatcct ttggtcagct gcccgcaacg      2820
tgcgatatac aatatacata ttttattatg ttttttttcgt gactaactat gttatcattt      2880
ttatagcttt atagtctaca aactgtttta tactcagctt gataagtaca ttctggtttg      2940
gacgattttt ttttcttgca aaatgaatt tgtcttcagc ctttacgact acatacagtt       3000
tagttcttag agtatctcat ctgtattaat tgataccgga agagattcgg gccacatata      3060
aacaaggaat atatagcacg tactcgctga accttaaata tagtcaggaa catagagggt      3120
taactaaacc gatccagaaa ccaattacat tgatattgac tctattcttc gtt            3173

<210> SEQ ID NO 8
<211> LENGTH: 3235
<212> TYPE: DNA
<213> ORGANISM: Zea mays

<400> SEQUENCE: 8
ggcaagctaa tggggtacat atggaaggag gaaaccaagt cgatcgtcgt cgtagcatgt       60
cggtgtgggt actacactac acacacatat acatgggcaa cgcaaggcca cctttctgaa      120
tcctgcatga gcgtgtacca ctagaattgt cagtgtgtgc ggtgtatggc aggttttggg      180
ttcggcaagt ggggccctcc ggggaggaat ctcagtaaca aaccgctctt ctgaaaaggt      240
cagccatccc cggtccggtc cggtgatgtc gtcgctgtcg ctctgctagc ttgctgccga      300
tccccccccc cccccccccc cttcttctct ctaccccctcc ctccacctca taaatactta      360
gtttaataac cttgcactgc cgcagtagcc cttaactgct gctatctatc tcttttctga      420
aggaaaaaaa aggtttgata ctcctctacc tagctagtcc tgcatgccgc taatgtgcgt      480
cttgcctgtt tatttgttct taataagggc tgcctatcta ttatattttg cacctgtttt      540
gctgtgttct tggtaactag cttaattcct ttgcctacaa tcgtcaaatc cccccccatca     600
tcagtcagat gaacttttga tcgaattgaa gttgttcttc taattcggcc ccagcagcgc     660
ccatgcatct ggttttattt gcttctgtt gggtataata tgcaagacct tttgttgcta      720
gggcaaggct gcaaccacat gcgtgtactg aactcatgat gtaactcatc ctttttgttt     780
gctcacagaa tcactactct actgcacttc cttttcatcc gatccgcaat cttttttttc     840
```

```
ttttacatgc tttagttttc tctctttctt gattacaaac atgattactg gaactttctt    900
aggctgcctt ccccttcctt ggatctgctt tagttttctt ttttgggcta ccgcgcgcgg    960
cttatttgag tttatcactt gctgcatata cataatatat atatacatgc atgcgatggc   1020
gttcatgtta ctcaactaca gatctgtttc tgttcgtgtg tttcagttca gcgcgcagtt   1080
aagcatagca ggacgaccac gacgatgtat cacccgcagt gcgagctcct gacgatggcg   1140
cacgaaacgc cggacctgga cgccggccag ccgcacctaa ccgtctccgg cgtcgccagc   1200
atcccggcag agctgagctt ccacctgctg cactcgctcg acgccgcggc ggcggtcaat   1260
cccgtcacgg cgccgccgca gtccaccatc gactacttcc tcggcggcgc cgatccccac   1320
cagcaggcca tgcagtacga gccgctgccg cccgccgcgg gcggccacca ccagtacacc   1380
atggacatgt tccgcgacta ctgcgacggc aactacccca ccgccgagcc gtacatccgc   1440
gggacaatga ctggagccct cgtgttcggg gccaccgacg acgacgactc ggccgctgcc   1500
gcctacatgc ccgggggggca cttttgagacc tccccgccgc cgccacgcgc caccggccgc   1560
ggcaggaagc ggggcagggc gctgggcggc ggcttccatg ctgtgctggc caacggcgtc   1620
gagaagaagg agaagcagcg ccggctgcgg ctcaccgaga agtttacggc cctcatgcac   1680
ctcataccca acgttacgaa ggtcgtacgg cgtacttgcg cgcggaccaa atcctcctct   1740
tatgttcgtc gtccatcgtc tcaaattaat tcacggttct tgttgttgtt tattttttgc   1800
gcactgcaga ctgatagggc gacggtgatc tcggacgcga tcgagtacat ccaggagctg   1860
gggaggacgg tggaggagct gacgctgctg gtggagaaga gcggcgccg gagggagctg   1920
caggggggacg tcgtggacgc ggcgccggct gcggtggttg ctgccgccgg tgaggcggag   1980
agctcggagg gcgaggtggc tcctccgccg ctggccgtgc cgcggcagcc gatccggagc   2040
acgtacatcc agcggcggag caaggacacg tccgtggacg tgcggatcgt ggaggaggac   2100
gtgaacatca agctcaccaa gcgccggcgc gacgggtgcc tcgcagccgc gtcgcgcgcg   2160
ctggacgacc tccgccttga cctcgtccac ctctccggcg gcaagatcgg tgactgtcaa   2220
atctacatgt tcaacaccaa ggtacatacg aatacgatac gtagccattg atcgatctgt   2280
aattctgtag cctgacgatt tcatgcatta cttttccgag gtttctgtgc tatactacct   2340
aacctaggtg ctaaaaaatg caccttttt tctcagatga caatgctttc tgtctttgtt   2400
caccgcagat tcacaagggg tcttcagtgt ttgcgagtgc agtggccggt aggctgatgg   2460
aagtggtgga cgagtactag gctaccatgc acttgaattt ctagctagct ctacgtaccg   2520
cgctgctatg aatctagcta tagcgttttct tggatgaaag aatagttagt tgttaccttc   2580
tatctttgct tcaattaaat ccgcttgctc gttacagact gagtttgttt ctaaatgtca   2640
aggttgtttt ggtcaaattg aataaattgg cacactggcc tgtgaggtta ttatatttat   2700
gtgtattatt actggtctat caatttgtcc tattattgta ttgcctgtca aggaataaat   2760
tgtatgatga tcatatttat gcatagatag gatgagtagg ttcacttgct tgagttcacc   2820
ggtataattc tggtttctgg atacatctgg ttaggtcagc ctttggtcag ctgcccgcaa   2880
gcttaactcc gtgcgatata cactatacaa attttattat gttttttcg tgactaacta   2940
tgttatcatt tttatagctt tatagtctac aaactgtttt atactcagct tgataagtac   3000
attctggttt ggacgatggt tttttttttc ttgcaaaaat gaatttgtct tcagccttta   3060
cgactacata cagtttagtt tgtattaatt gataccagaa gatcagattc ggaccacata   3120
taaacaagga atatatagca cgtactcgct gaaccttaaa tatagtcagg aacatagagg   3180
gttaactaaa ccgatccaga aaccaattac attgatattg actctattct tcgtt        3235
```

<210> SEQ ID NO 9
<211> LENGTH: 3235
<212> TYPE: DNA
<213> ORGANISM: Zea mays

<400> SEQUENCE: 9

| | | | | | |
|---|---|---|---|---|---|
| ggcaagctaa | tggggtacat | atggaaggag | gaaaccaagt | cgatcgtcgt | cgtagcatgt | 60 |
| cggtgtgggt | actacactac | acacacatat | acatgggcaa | cgcaaggcca | cctttctgaa | 120 |
| tcctgcatga | gcgtgtacca | ctagaattgt | cagtgtgtgc | ggtgtatggc | aggttttttgg | 180 |
| ttcggcaagt | ggggccctcc | ggggaggaat | ctcagtaaca | aaccgctctt | ctgaaaaggt | 240 |
| cagccatccc | cggtccggtc | cggtgatgtc | gtcgctgtcg | ctctgctagc | ttgctgccga | 300 |
| tccccccccc | ccccccccc | cttcttctct | ctacccctcc | ctccacctca | taaatactta | 360 |
| gtttaataac | cttgcactgc | cgcagtagcc | cttaactgct | gctatctatc | tcttttctga | 420 |
| aggaaaaaaa | aggtttgata | ctcctctacc | tagctagtcc | tgcatgccgc | taatgtgcgt | 480 |
| cttgcctgtt | tatttgttct | taataagggc | tgcctatcta | ttatattttg | cacctgtttt | 540 |
| gctgtgttct | tggtaactag | cttaattcct | ttgcctacaa | tcgtcaaatc | cccccccatca | 600 |
| tcagtcagat | gaacttttga | tcgaattgaa | gttgttcttc | taattcggcc | ccagcagcgc | 660 |
| ccatgcatct | ggttttattt | gctttctgtt | gggtataata | tgcaagacct | tttgttgcta | 720 |
| gggcaaggct | gcaaccacat | gcgtgtactg | aactcatgat | gtaactcatc | cttttttgttt | 780 |
| gctcacagaa | tcactactct | actgcacttc | cttttcatcc | gatccgcaat | cttttttttc | 840 |
| ttttacatgc | tttagttttc | tctctttctt | gattacaaac | atgattactg | gaactttctt | 900 |
| aggctgcctt | cccttccctt | ggatctgctt | tagttttctt | ttttgggcta | ccgcgcgcgg | 960 |
| cttatttgag | tttatcactt | gctgcatata | cataatatat | atatacatgc | atgcgatggc | 1020 |
| gttcatgtta | ctcaactaca | gatctgtttc | tgttcgtgtg | tttcagttca | gcgcgcagtt | 1080 |
| aagcatagca | ggacgaccac | gacgatgtat | cacccgcagt | gcgagctcct | gacgatggcg | 1140 |
| cacgaaacgc | cggacctgga | cgccggccag | ccgcacctaa | ccgtctccgg | cgtcgccagc | 1200 |
| atcccggcag | agctgagctt | ccacctgctg | cactcgctcg | acgccgcggc | ggcggtcaat | 1260 |
| cccgtcacgg | cgccgccgca | gtccaccatc | gactacttcc | tcggcggcgc | cgatccccac | 1320 |
| cagcaggcca | tgcagtacga | gccgctgccg | cccgccgcgg | gcggccacca | ccagtacacc | 1380 |
| atggacatgt | tccgcgacta | ctgcgacggc | aactacccca | ccgccgagcc | gtacatccgc | 1440 |
| gggacaatga | ctggagccct | cgtgttcggg | gccaccgacg | acgacgactc | ggccgctgcc | 1500 |
| gcctacatgc | ccgggggggca | ctttgagacc | tccccgccgc | cgccacgcgc | caccggccgc | 1560 |
| ggcaggaagc | ggggcagggc | gctggccggc | ggcttccatg | ctgtgctggc | caacggcgtc | 1620 |
| gagaagaagg | agaagcagcg | ccggctgcgg | ctcaccgaga | agtttacggc | cctcatgcac | 1680 |
| ctcataccca | acgttacgaa | ggtcgtacgg | cgtacttgcg | cgcggaccaa | atcctcctct | 1740 |
| tatgttcgtc | gtccatcgtc | tcaaattaat | tcacggttct | tgttgttgtt | tattttttgc | 1800 |
| gcactgcaga | ctgatagggc | gacggtgatc | tcggacgcga | tcgagtacat | ccaggagctg | 1860 |
| gggaggacgg | tggaggagct | gacgctgctg | gtggagaaga | agcggcgccg | gagggagctg | 1920 |
| caggggggacg | tcgtggacgc | ggcgccggct | gcggtggttg | ctgccgccgg | tgaggcggag | 1980 |
| agctcggagg | gcgaggtggc | tcctccgccg | ctggccgtgc | cgcggcagcc | gatccggagc | 2040 |
| acgtacatcc | agcggcggag | caaggacacg | tccgtggacg | tgcggatcgt | ggaggaggac | 2100 |

-continued

| | | |
|---|---|---|
| gtgaacatca agctcaccaa gcgccggcgc gacgggtgcc tcgcagccgc gtcgcgcgcg | 2160 |
| ctggacgacc tccgccttga cctcgtccac ctctccggcg gcaagatcgg tgactgtcaa | 2220 |
| atctacatgt tcaacaccaa ggtacatacg aatacgatac gtagccattg atcgatctgt | 2280 |
| aattctgtag cctgacgatt tcatgcatta cttttccgag gtttctgtgc tatactacct | 2340 |
| aacctaggtg ctaaaaaatg cacctttttt tctcagatga caatgctttc tgtctttgtt | 2400 |
| caccgcagat tcacaagggg tcttcagtgt ttgcgagtgc agtggccggt aggctgatgg | 2460 |
| aagtggtgga cgagtactag gctaccatgc acttgaattt ctagctagct ctacgtaccg | 2520 |
| cgctgctatg aatctagcta tagcgtttct tggatgaaag aatagttagt tgttaccttc | 2580 |
| tatctttgct tcaattaaat ccgcttgctc gttacagact gagtttgttt ctaaatgtca | 2640 |
| aggttgtttt ggtcaaattg aataaattgg cacactggcc tgtgaggtta ttatatttat | 2700 |
| gtgtattatt actggtctat caatttgtcc tattattgta ttgcctgtca aggaataaat | 2760 |
| tgtatgatga tcatatttat gcatagatag gatgagtagg ttcacttgct tgagttcacc | 2820 |
| ggtataattc tggtttctgg atacatctgg ttaggtcagc ctttggtcag ctgcccgcaa | 2880 |
| gcttaactcc gtgcgatata cactatacaa attttattat gttttttttcg tgactaacta | 2940 |
| tgttatcatt tttatagctt tatagtctac aaactgtttt atactcagct tgataagtac | 3000 |
| attctggttt ggacgatggt tttttttttc ttgcaaaaat gaatttgtct tcagccttta | 3060 |
| cgactacata cagtttagtt tgtattaatt gataccagaa gatcagattc ggaccacata | 3120 |
| taaacaagga atatatagca cgtactcgct gaaccttaaa tatagtcagg aacatagagg | 3180 |
| gttaactaaa ccgatccaga aaccaattac attgatattg actctattct tcgtt | 3235 |

<210> SEQ ID NO 10
<211> LENGTH: 3235
<212> TYPE: DNA
<213> ORGANISM: Zea mays

<400> SEQUENCE: 10

| | | |
|---|---|---|
| ggcaagctaa tggggtacat atggaaggag gaaaccaagt cgatcgtcgt cgtagcatgt | 60 |
| cggtgtgggt actacactac acacacatat acatgggcaa cgcaaggcca cctttctgaa | 120 |
| tcctgcatga gcgtgtacca ctagaattgt cagtgtgtgc ggtgtatggc aggttttttgg | 180 |
| ttcggcaagt ggggccctcc ggggaggaat ctcagtaaca aaccgctctt ctgaaaaggt | 240 |
| cagccatccc cggtccggtc cggtgatgtc gtcgctgtcg ctctgctagc ttgctgccga | 300 |
| tccccccccc ccccccccc cttcttctct ctaccctcc ctccacctca taaatactta | 360 |
| gtttaataac cttgcactgc cgcagtagcc cttaactgct gctatctatc tcttttctga | 420 |
| aggaaaaaaa aggtttgata ctcctctacc tagctagtcc tgcatgccgc taatgtgcgt | 480 |
| cttgcctgtt tatttgttct taataagggc tgcctatcta ttatattttg cacctgtttt | 540 |
| gctgtgttct tggtaactag cttaattcct ttgcctacaa tcgtcaaatc cccccatca | 600 |
| tcagtcagat gaacttttga tcgaattgaa gttgttcttc taattcggcc ccagcagcgc | 660 |
| ccatgcatct ggtttttattt gctttctgtt gggtataata tgcaagacct tttgttgcta | 720 |
| gggcaaggct gcaaccacat gcgtgtactg aactcatgat gtaactcatc cttttgtttt | 780 |
| gctcacagaa tcactactct actgcacttc cttttcatcc gatccgcaat cttttttttc | 840 |
| ttttacatgc tttagttttc tctctttctt gattacaaac atgattactg gaactttctt | 900 |
| aggctgcctt ccccttcctt ggatctgctt tagttttctt ttttgggcta ccgcgcgcgg | 960 |
| cttatttgag tttatcactt gctgcatata cataatatat atatacatgc atgcgatggc | 1020 |

-continued

```
gttcatgtta ctcaactaca gatctgtttc tgttcgtgtg tttcagttca gcgcgcagtt      1080
aagcatagca ggacgaccac gacgatgtat cacccgcagt gcgagctcct gacgatggcg      1140
cacgaaacgc cggacctgga cgccggccag ccgcacctaa ccgtctccgg cgtcgccagc      1200
atcccggcag agctgagctt ccacctgctg cactcgctcg acgccgcggc ggcggtcaat      1260
cccgtcacgg cgccgccgca gtccaccatc gactacttcc tcggcggcgc cgatccccac      1320
cagcaggcca tgcagtacga gccgctgccg cccgccgcgg gcggccacca ccagtacacc      1380
atggacatgt ccgcgactac tgcgacggc aactacccca ccgccgagcc gtacatccgc      1440
gggacaatga ctggagccct cgtgttcggg gccaccgacg acgacgactc ggccgctgcc      1500
gcctacatgc ccggggggca ctttgagacc tccccgccgc cgccacgcgc caccggccgc      1560
ggcaggaagc ggggcagggc gctgggcggc ggcttccatg ctgtgctggc caacggcgtc      1620
gagaagaagg agaagcagcg ccggctgcgg ctcaccgaga agtttacggc cctcatgcac      1680
ctcatacccc acgttacgaa ggtcgtacgg cgtacttgcg cgcggaccaa atcctcctct      1740
tatgttcgtc gtccatcgtc tcaaattaat tcacggttct tgttgttgtt tattttttgc      1800
gcactgcaga ctgataggc gacggtgatc tcggacgcga tcgagtacat ccaggagctg      1860
gggaggacgg tggaggagct gacgctgctg gtggagaaga agcggcgccg gagggagctg      1920 caggggacg tcgtggacgc ggcgccggct gcggtggttg ctgccgccgg tgaggcggag      1980
agctcggagg gcgaggtggc tcctccgccg ctggccgtgc cgcggcagcc gatccggagc      2040
acgtacatcc agcggcggag caaggacacg tccgtggacg tgcggatcgt ggaggaggac      2100
gtgaacatca agctcaccaa gcgccggcgc gacgggtgcc tcgcagccgc gtcgcgcgcg      2160
ctggacgacc tccgccttga cctcgtccac ctctccggcg gcaagatcgg tgactgtcaa      2220
atctacatgt tcaacaccaa ggtacatacg aatacgatac gtagccattg atcgatctgt      2280
aattctgtag cctgacgatt tcatgcatta cttttccgag gtttctgtgc tatactacct      2340
aacctaggtg ctaaaaaatg cacctttttt tctcagatga caatgctttc tgtctttgtt      2400
caccgcagat tcacaagggg tcttcagtgt ttgcgagtgc agtggccggt aggctgatgg      2460
aagtggtgga cgagtactag gctaccatgc acttgaattt ctagctagct ctacgtaccg      2520
cgctgctatg aatctagcta tagcgtttct tggatgaaag aatagttagt tgttaccttc      2580
tatctttgct tcaattaaat ccgcttgctc gttacagact gagtttgttt ctaaatgtca      2640
aggttgtttt ggtcaaattg aataaattgg cacactggcc tgtgaggtta ttatatttat      2700
gtgtattatt actggtctat caatttgtcc tattattgta ttgcctgtca aggaataaat      2760
tgtatgatga tcatatttat gcatagatag gatgagtagg ttcacttgct tgagttcacc      2820
ggtataattc tggtttctgg atacatctgg ttaggtcagc cttggtcag ctgcccgcaa      2880 gcttaactcc gtgcgatata cactatacaa attttattat gttttttcg tgactaacta      2940 tgttatcatt tttatagctt tatagtctac aaactgtttt atactcagct tgataagtac      3000
attctggttt ggacgatggt ttttttttc ttgcaaaaat gaatttgtct tcagccttta      3060
cgactacata cagtttagtt tgtattaatt gataccagaa gatcagattc ggaccacata      3120
taaacaagga atatatagca cgtactcgct gaaccttaaa tatagtcagg aacatagagg      3180
gttaactaaa ccgatccaga aaccaattac attgatattg actctattct tcgtt           3235
```

<210> SEQ ID NO 11
<211> LENGTH: 19
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 11
caacggcgtc gagaagaag                                                    19

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctcggcgtcg gccgcgacga agag                                              24

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
accgagaagt acaccgc                                                      17

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
attgcaaccc atactccacg ta                                                22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caacggcgtc gagaagaag                                                    19

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcggcgtcgg ccgcgacgaa gag                                               23

<210> SEQ ID NO 17
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      probe

<400> SEQUENCE: 17
caccgagaag tttacggc                                                        18

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
attgcaaccc atactccacg ta                                                   22
```